United States Patent
Sharkey et al.

(10) Patent No.: US 10,660,759 B2
(45) Date of Patent: May 26, 2020

(54) SET OF SURGICAL INSTRUMENTS FOR AN ARTIFICIAL HIP JOINT IMPLANT

(71) Applicant: Corentec Co., LTD., Cheonan-si, Chungcheongnam-do (KR)

(72) Inventors: Peter F. Sharkey, Villanova, PA (US); Javad Parvizi, Gladwyne, PA (US)

(73) Assignee: Corentec Co., Ltd., Cheonan-si, Chungcheongnam-Do (KR)

( * ) Notice: Subject to any disclaimer, the term of this patent is extended or adjusted under 35 U.S.C. 154(b) by 286 days.

(21) Appl. No.: 15/661,738

(22) Filed: Jul. 27, 2017

(65) Prior Publication Data

US 2018/0028196 A1  Feb. 1, 2018

Related U.S. Application Data

(60) Provisional application No. 62/367,908, filed on Jul. 28, 2016.

(51) Int. Cl.

| | |
|---|---|
| *A61F 2/34* | (2006.01) |
| *A61F 2/30* | (2006.01) |
| *A61F 2/46* | (2006.01) |
| *A61B 17/16* | (2006.01) |
| *A61B 90/00* | (2016.01) |
| *A61B 17/14* | (2006.01) |
| *A61B 17/02* | (2006.01) |
| *A61B 17/15* | (2006.01) |
| *A61B 17/92* | (2006.01) |
| *A61F 2/32* | (2006.01) |
| *A61B 17/00* | (2006.01) |
| *A61B 17/17* | (2006.01) |

(52) U.S. Cl.
CPC .............. *A61F 2/34* (2013.01); *A61B 17/025* (2013.01); *A61B 17/0218* (2013.01); *A61B 17/149* (2016.11); *A61B 17/15* (2013.01); *A61B 17/1613* (2013.01); *A61B 17/1631* (2013.01); *A61B 17/1659* (2013.01); *A61B 17/1664* (2013.01); *A61B 17/1668* (2013.01); *A61B 17/92* (2013.01); *A61B 90/06* (2016.02); *A61F 2/30724* (2013.01); *A61F 2/4637* (2013.01); *A61B 17/1633* (2013.01); *A61B 17/1742* (2013.01); *A61B 2017/00876* (2013.01); *A61B 2017/00991* (2013.01); *A61B 2017/0275* (2013.01); *A61B 2017/922* (2013.01); *A61B 2090/064* (2016.02); *A61F 2002/30565* (2013.01); *A61F 2002/30617* (2013.01); *A61F 2002/30718* (2013.01); *A61F 2002/30719* (2013.01); *A61F 2002/3208* (2013.01); *A61F 2002/348* (2013.01); *A61F 2002/4666* (2013.01)

(58) Field of Classification Search
CPC ........................ A61B 17/1659; A61B 17/1668
See application file for complete search history.

(56) References Cited

U.S. PATENT DOCUMENTS

2011/0160733 A1*  6/2011  Wallstein ........... A61B 17/1659
                                                       606/85

* cited by examiner

*Primary Examiner* — Olivia C Chang
(74) *Attorney, Agent, or Firm* — Workman Nydegger

(57) ABSTRACT

A set of surgical instruments for an artificial hip joint implant and, more specifically, a set of improved surgical instruments, can be used in direct anterior approach hip replacement surgery and are capable of minimizing damage, such as muscle damage, which may arise during surgery, by resolving problems that existing surgical instruments possess.

7 Claims, 35 Drawing Sheets

SET OF SURGICAL INSTRUMENTS FOR AN ARTIFICIAL HIP JOINT IMPLANT

CROSS-REFERENCE TO RELATED APPLICATIONS

This application claims the benefit of U.S. Provisional Application No. 62/367,908, filed Jul. 28, 2016, which is incorporated herein by specific reference.

TECHNICAL FIELD

The present invention relates to a set of surgical instruments for an artificial hip joint implant and, more specifically, to a set of improved surgical instruments which can be used in direct anterior approach hip replacement surgery, capable of minimizing damage, such as muscle damage, which may arise during surgery, by resolving problems that existing surgical instruments possess.

BACKGROUND

Direct anterior hip replacement surgery, a type of total hip arthroplasty, is a minimally invasive surgical technique. With the direct anterior approach, surgery is performed through a natural space between the muscles of the anterior portion of the hip, rather than making the incision on the posterior side. That is, the hip joint is exposed between the anterior muscles without a need to separate tendons or cut tissues during this procedure. The portion of the upper thigh bone which includes the femoral head and neck and the hip socket which includes acetabulum are prepared for the insertion of the hip replacement implant once access to the hip joint is accomplished. The direct anterior approach has advantages in that damage of muscles or pain is decreased and healing time is relatively faster compared to posterior approach.

Various surgical instruments, such as a retractor, a starter reamer, and a broach, are used in the direct anterior approach total hip replacement surgery. Each of these instruments needs improvements to increase surgical efficiency in the direct anterior approach surgery. Necessary improvements are followed below.

I. Retractor and Saw

In total hip arthroplasty, different types of a saw, such as a power saw and a gigli saw, are being used to cut the femur, and a surgical instrument called a retractor is inserted in a surgical area and separates the surgical area by fixing surrounding muscles for preventing damage of the surrounding muscles. FIGS. 1a and 1b show a perspective view of and a top view of a retractor fixed for femoral resection where capsule 402 around a head of the femur 404 remains intact during direct anterior approach surgery.

When the power saw is used to cut a neck of the femur in the direct anterior approach, posterior capsule 402 is not resected and remains even after the neck of the femur 404 is resected. In this case, the head part of the femur 404 cannot be exposed. Removing the posterior capsule constitutes one of the most challenging steps in direct anterior approach surgery due to limited access and bleeding from femoral canal. Therefore, the gigli saw (not shown) may be used to solve such problem by simultaneously resecting the neck of the femur 404 and the surrounding capsule 402. However, delimiting an area to be resected is not simple and damage of surrounding muscles may occur even when the gigli saw is used.

Accordingly, there is a need to develop an instrument capable of minimizing damage to the surrounding muscles, facilitating delimitation of the area to be resected, and relatively easily resecting the neck and the capsule simultaneously.

In addition, as shown in FIGS. 1a and 1b, two retractors 406 are disposed facing with each other to separate the surgical area in the direct anterior approach surgery. Currently, fixing of the two retractors 406 is done by manpower. This additional manpower reduces surgical efficiency.

Therefore, there remains a need to develop a surgical instrument which can improve surgical efficiency by fixing the retractor in a different way without the need of additional manpower.

Moreover, muscle trauma (specifically TFL and gluteal muscles) is common when the direct anterior approach surgery is performed on a large, muscular patient. This damage usually occurs due to retractors or instruments used to prepare the femur for implant. Especially, prior narrow retractors place high force on a small area of the muscle and pull the muscle in direct contact, which becomes a major cause for muscle damage.

Hence, it is necessary to improve retractors to minimize damage to the surrounding muscle.

II. Starter Reamer

A starter reamer is used to enlarge a hole for inserting a femoral stem in direct anterior approach total hip replacement. The starter reamer has sharp teeth and a tough shaft. The sharp teeth are provided in a portion of the starter reamer, encountering the muscle in a moving path of the starter reamer, thereby causing muscle damage during the insertion process.

Accordingly, an improvement is required to prevent muscle damage when the starter reamer is inserted.

III. Broach

An artificial joint is placed between the femur and the pelvis in total hip arthroplasty, for which a surgical portion recessed by a certain size in the femur is formed to insert and fix the artificial joint. The surgical instrument used in this case is a broach.

The broach is coupled to a broach handle gripped by an operator. The terms of the broach and the broach handle are used interchangeably with a rasp and a rasp handle in the relevant industry. The broach and the broach handle will be used in the present disclosure.

Generally, a broach having a shape similar to the shape of a stem is used after the use of the starter reamer. Since the broach has sharp teeth, there is potential risk that the broach causes damage to the muscles when being inserted into a human body to create the surgical portion in the femur. Specifically, one part of the broach which is inserted in the bone does not damage the muscle, but another part of the broach which is exposed to the outside of the bone and contacts with the muscle causes muscle damage.

Therefore, the broach needs improvement to be safely used without causing muscle damage.

IV. Trunnion

Exposure of a trunnion of the femoral stem to the outside should be kept to a minimum until the femoral stem is completely inserted into the human body and the ball head is connected. Currently, the trunnion preparation is compromised by limited exposure, contamination by water insoluble substances and residual cloth fibers remaining after drying with sponges.

Therefore, an instrument capable of protecting the trunnion is needed.

V. Impaction Force

When a modular head is inserted in the hip joint, too much impaction force might cause fracture of the modular head, while too weak impaction force brings about a risk of premature separation after surgery. Thus, surgical failure rate can be decreased if the amount of impaction force to be applied in actual surgery can be measured before the insertion of the modular head. However, a device for quantitatively measuring the impaction force has not yet appeared.

Accordingly, there is a need to develop improved surgical instruments used in the direct anterior approach hip replacement surgery to resolve the abovementioned issues.

SUMMARY OF THE INVENTION

Technical Problem

The present invention has been made in an effort to solve the problems.

An object of the present invention is to provide a set of improved surgical instruments used in the direct anterior approach hip replacement surgery.

Another object of the present invention is to provide a set of surgical instruments for an artificial hip joint implant, capable of preventing muscle damage by delimiting an area to be resected when a femoral neck and surrounding capsule thereof are simultaneously resected using a gigli saw in the direct anterior approach.

Yet another object of the present invention is to provide a set of surgical instruments for an artificial hip joint implant comprising an instrument capable of stably fixing a retractor.

Yet another object of the present invention is to provide a set of surgical instruments for an artificial hip joint implant comprising a retractor capable of reducing muscle damage.

Yet another object of the present invention is to provide a set of surgical instruments for an artificial hip joint implant comprising a reamer capable of minimizing muscle damage.

Yet another object of the present invention is to provide a set of surgical instruments for an artificial hip joint implant comprising a broach capable of minimizing muscle damage.

Yet another object of the present invention is to provide a surgical instrument for an artificial hip joint implant comprising an instrument capable of protecting a trunnion of a femoral stem from external contaminants.

Yet another object of the present invention is to provide an impaction measuring device designed to measure in advance the impaction applied to a modular head in actual surgery.

Technical Solutions

The present invention has been made in an effort to solve the problems.

According to the present invention, a set of surgical instruments for an artificial hip joint implant comprises a pair of retractors disposed to face with each other for fixing skin and muscles around a surgical portion of a hip joint; and a tubular element disposed a certain gap apart from the retractors and having at least part identically shaped with the surface shape of the retractors, wherein a slit is formed in the tubular element for passing a gigli saw inserted in the gap.

According to another embodiment of the present invention, the slit is formed along the at least part of the tubular element, formed identically to the surface shape of the retractors.

According to yet another embodiment of the present invention, the slit is formed such that the slit is parallel to a resection line of a femoral neck.

According to yet another embodiment of the present invention, the slit is formed along the longitudinal direction of the tubular element, and both ends of the slit are expanded in a direction substantially perpendicular to the longitudinal direction of the tubular element.

According to yet another embodiment of the present invention, the retractors comprise a grip portion to be gripped, respectively, and the grip portions are connected to each other by a bar member.

According to yet another embodiment of the present invention, a mounting hole is formed in the grip portion and a coupling hole is formed at both sides of the bar member to fix the grip portion and the bar member by fastening the mounting hole and the coupling hole by a coupling member.

According to yet another embodiment of the present invention, the grip portion and the bar member comprise a plurality of mounting holes and coupling holes, respectively, and the coupling position of the mounting hole and the coupling hole is changed such that the distance between the retractors is adjustable.

According to yet another embodiment of the present invention, the retractors comprise a fixing part which fixes muscle by being inserted in the surgical portion and each of the fixing parts is formed by a magnet with an opposite polarity.

According to yet another embodiment of the present invention, the retractor comprises a shield formed to expand contact area with the surrounding muscle and extending to both sides of the retractor, and edges of the shield are rounded.

According to yet another embodiment of the present invention, the shield is movably fixed in the retractor.

According to yet another embodiment of the present invention, a set of surgical instruments for an artificial hip joint implant comprises: a reamer forming a hole for installing a femoral stem in a femur; and a telescopic protector disposed to surround an outer circumference of the reamer.

According to yet another embodiment of the present invention, the telescopic protector comprises: a first rod disposed to surround a front portion of the reamer and having a first penetration hole penetrating the longitudinal direction; and a second rod slidably coupled to the outer circumference of the first rod and having an inner diameter substantially the same with an outer diameter of the first rod and a second penetration hole penetrating the longitudinal direction, wherein the first rod is configured to enter an inner side of the second rod as the reamer advances.

According to yet another embodiment of the present invention, the telescopic protector further comprises a third rod slidably coupled to the outer circumference of the second rod and having an inner diameter substantially the same with an outer diameter of the second rod and a third penetration hole penetrating the longitudinal direction, wherein the second rod is configured to enter an inner side of the third rod as the reamer advances.

According to yet another embodiment of the present invention, a set of surgical instruments for an artificial hip joint implant comprises a reamer forming a hole for a femoral stem in a femur, wherein the reamer includes a cutting portion having cutting edges on the outer circumferential face and a shaft connected to the cutting portion, and the shaft is formed by flexible material.

According to yet another embodiment of the present invention, a set of surgical instruments for an artificial hip joint implant comprises a broach for enlarging a hole for installing a femoral stem in a femur, wherein the broach comprises a modular broach including a plurality of cutting segments and a guide portion guiding the plurality of the cutting segments.

According to yet another embodiment of the present invention, the modular broach comprises: a guide member; a first cutting segment installed at an end of the guide member and having a wedge shape and cutting edges; and a second cutting segment formed movably along the guide member to be disposed at a rear side of the first cutting segment and having cutting edges on the outer circumference.

According to yet another embodiment of the present invention, the second cutting segment has a shape of a circular truncated cone.

According to yet another embodiment of the present invention, the modular broach comprises: a guide member; and a first cutting segment installed at one side of the guide member, wherein the first cutting segment includes a first cutout portion in which at least part of the volume at an upper side of the first cutting segment is cut out.

According to yet another embodiment of the present invention, the guide member and the first cutting segment are coupled by screw connection along a horizontal direction.

According to yet another embodiment of the present invention, a shape of the circumference of the first cutout portion is formed substantially the same with a shape of the circumference of the guide member and the circumferences include a straight portion.

According to yet another embodiment of the present invention, a protrusion receiving portion is formed in a part where the first cutout portion contacts with the first cutting segment.

According to yet another embodiment of the present invention, the set of surgical instruments further comprises: an auxiliary guide member connected to the guide member; and a second cutting segment installed in the auxiliary guide member, wherein the second cutting segment includes a second cutout portion where at least part of the volume of the second cutting segment is cut out at an upper part of the second cutting segment and the guide member is received in the second cutout portion.

According to yet another embodiment of the present invention, the second cutting segment includes a protrusion protruding in a lower part of the second cutting segment.

According to yet another embodiment of the present invention, the guide member and the auxiliary guide member are coupled by a coupling member and the coupling member is mounted on an upper face of the second cutting segment and includes an insertion hole at one side and a slot formed at the other side, wherein the slot has one side open to receive the guide member.

According to yet another embodiment of the present invention, an end of the auxiliary guide member has a hemispherical shape and is coupled to a hole formed in the second cutting segment.

According to yet another embodiment of the present invention, a set of surgical instruments for an artificial hip joint implant comprises: a trunnion protector having a shape of a cone and surrounding an outer face of the trunnion for protecting a trunnion of a femoral stem.

According to yet another embodiment of the present invention, the trunnion protector has a receiving portion for receiving the stem in an inner face, wherein the receiving portion has a complementary shape to a shape of the femoral stem for fit connection.

According to yet another embodiment of the present invention, a cutting line is formed in an outer face of the trunnion protector such that cutting for separating the protector is facilitated.

According to yet another embodiment of the present invention, a set of surgical instruments for an artificial hip joint implant comprises an impaction measuring device, including: a main body; a resisting body received inside the main body; and an impactor connected to an end of the resisting body, the impactor and the resisting body are connected to each other to be movable together by an impaction force in a direction of the impaction force applied.

According to yet another embodiment of the present invention, wherein the main body includes: a base portion; and a cylinder portion protruding perpendicularly with respect to the base portion and having a through-hole inside.

According to yet another embodiment of the present invention, the resisting body is received inside the through-hole, one end of the resisting body is connected to the base portion and the other end of the resisting body is connected to the impactor.

According to yet another embodiment of the present invention, the impactor includes: a strike portion to which an impaction force is applied; and a rod portion formed perpendicularly to the strike portion.

According to yet another embodiment of the present invention, a display means displaying the level of the applied impaction force is formed on a surface of the rod portion.

Advantageous Effect

According to embodiments of the present invention, the present invention can obtain the following effects.

According to the present invention, provided is a set of improved surgical instruments used in the direct anterior approach hip replacement surgery.

According to the present invention, provided is a set of surgical instruments for an artificial hip joint implant, capable of preventing muscle damage by delimiting an area to be resected when a femoral neck and surrounding capsule thereof are simultaneously resected using a gigli saw in the direct anterior approach.

According to the present invention, provided is a set of surgical instruments for an artificial hip joint implant comprising an instrument capable of stably fixing a retractor.

According to the present invention, provided is a set of surgical instruments for an artificial hip joint implant comprising a retractor capable of reducing muscle damage.

According to the present invention, provided is a set of surgical instruments for an artificial hip joint implant comprising a reamer capable of minimizing muscle damage.

According to the present invention, provided is a set of surgical instruments for an artificial hip joint implant comprising a broach capable of minimizing muscle damage.

According to the present invention, provided is a surgical instrument for an artificial hip joint implant, comprising an instrument capable of protecting a trunnion of a femoral stem from external contaminants.

According to the present invention, provided is an impaction measuring device designed to measure in advance the impaction applied to a modular head in actual surgery.

BEST DESCRIPTION OF THE DRAWINGS

FIG. 1b is a top view of FIG. 1a;

FIG. 37c shows a bottom view of a trunnion protector of FIG. 37a;

DETAILED DESCRIPTION

Figure 1A:
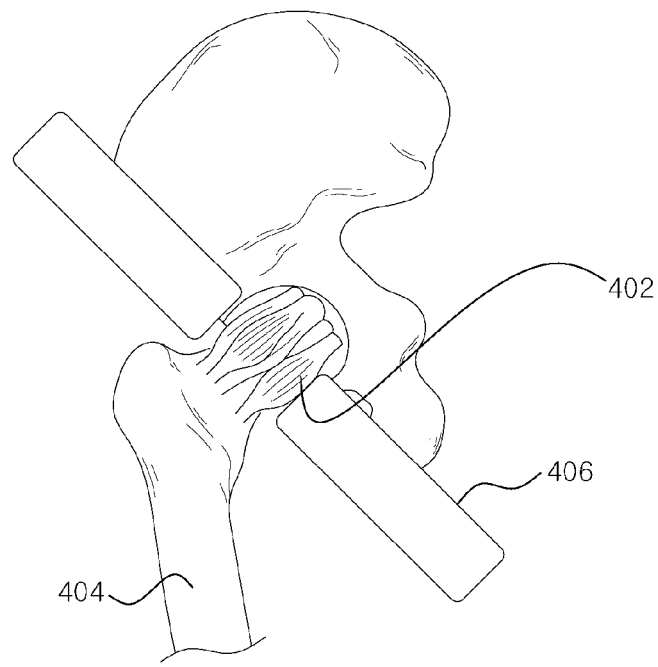
FIG. 1a illustrates a view of a retractor fixed in a femur for resection in direct anterior total hip arthroplasty.
Figure 1B:
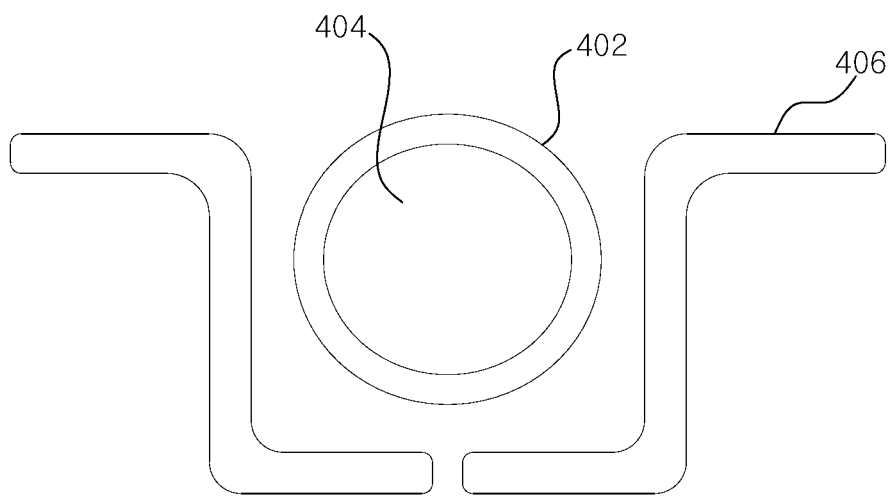

Hereinafter, a set of surgical instruments for an artificial hip joint implant according to the present invention is described in detail. Well-known functions or constructions will not be described in detail in case they may unnecessarily obscure the understanding of the present invention.

Specific structural and functional descriptions of embodiments of the present invention disclosed herein are only for illustrative purposes of the embodiments of the present invention. The embodiments according to the spirit and scope of the present invention can be variously modified in many different forms. While the present invention will be described in conjunction with exemplary embodiments thereof, it is to be understood that the present description is not intended to limit the present invention to those exemplary embodiments. On the contrary, the present invention is intended to cover not only the exemplary embodiments, but also various alternatives, modifications, equivalents and other embodiments that may be included within the spirit and scope of the present invention as defined by the appended claims.

The same reference numerals represent the same elements throughout the specification. It will be further understood that the terms "comprise", "include", "have", etc. when used in this specification, specify the presence of stated features, integers, steps, operations, elements, components, and/or combinations of them but do not preclude the presence or addition of one or more other features, integers, steps, operations, elements, components, and/or combinations thereof.

Below exemplary embodiments of the present invention are described in detail with reference to accompanying drawings. The invention may, however, be embodied in many different forms and should not be construed as being limited to the embodiments set forth herein; rather, these embodiments are provided so that this disclosure will be thorough and complete, and will fully convey the concept of the invention to those skilled in the art.

The present invention directed to surgical instruments for direct anterior approach hip replacement surgery is designed to resolve issues that existing surgical instruments used in the direct anterior approach surgery possess. To this end, the surgical instruments for an artificial hip joint implant according to the present invention may comprise: a retractor, a reamer, a broach, a trunnion protector and an impaction measuring device.

The retractor according to the present invention is now described in detail below. The retractor according to the present invention may comprise: at least one of a tubular element and a fixing means for fixing the retractor.

The retractor is a surgical instrument used to fix the skin and muscles around the surgical portion of the hip joint. For instance, the retractor assists in resecting the femoral neck by separating the femur from the surrounding muscles when the resection of the femoral neck is performed. As described above, a gigli saw may be used such that posterior capsules do not remain after resection of the femoral neck in the direct anterior approach. Due to some characteristics of the gigli saw, such as the shape and an inserting position, delimitation of the area to be resected may be difficult or damage to the surrounding muscles may be accompanied.

Figure 2:
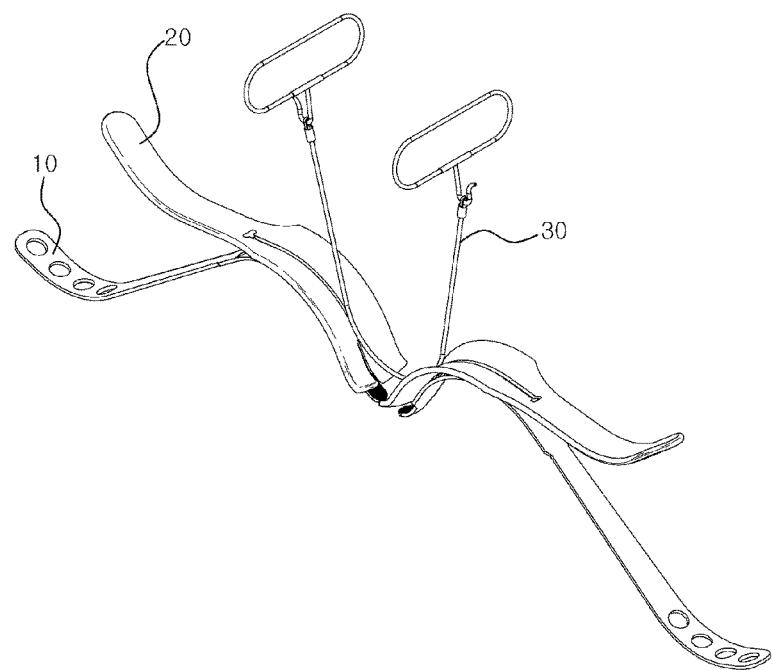
FIG. 2 shows a perspective view of a retractor having a tubular element according to an embodiment of the present invention.
Figure 3:
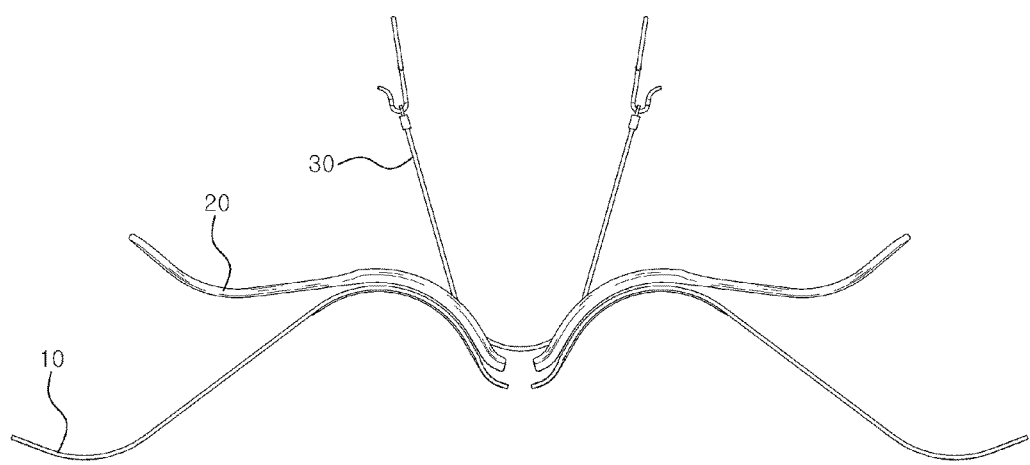
FIG. 3 shows one side view of FIG. 2.

As shown in FIGS. 2 and 3, a set of surgical instruments for an artificial hip joint implant according to one embodiment of the present invention may comprise a retractor 10 including a tubular element 20. The tubular element 20 is designed to prevent damage to the surrounding muscles by delimiting the area to be resected when the femoral neck and the surrounding capsules are simultaneously resected, using the gigli saw 30 in the direct anterior approach surgery, and by guiding the gigli saw 30. In the drawings, specific types of retractors 10 are illustrated, only to which the shape is not limited, but various types of retractors can be used.

Figure 4:
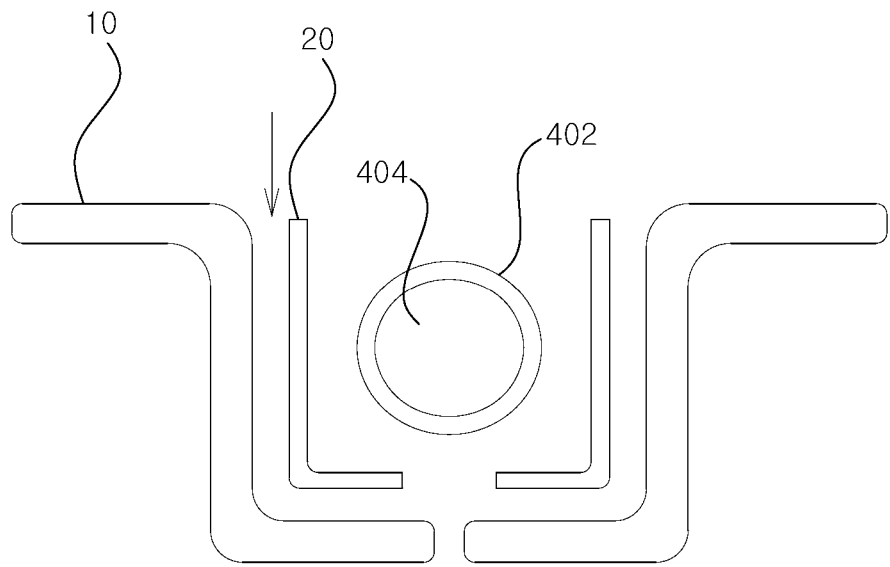
FIGS. 4 to 6 are conceptualized views of FIG. 3.
Figure 5:
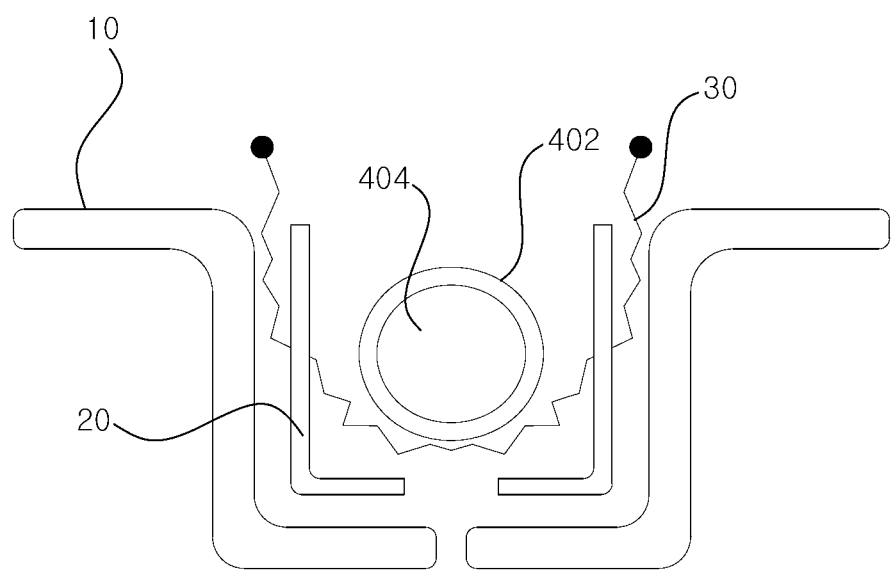
Figure 6:
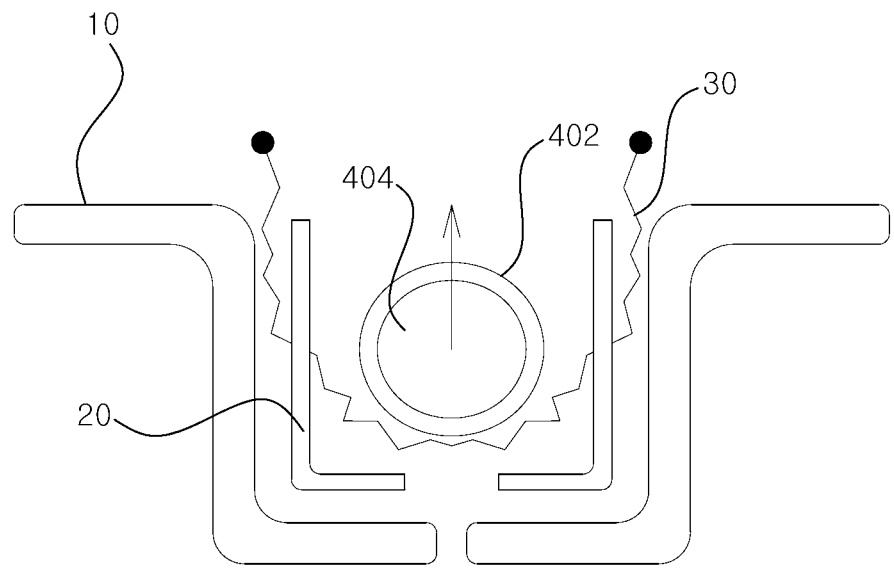

FIG. 4 to FIG. 6 illustrate conceptual views of FIG. 3. The retractor 10 is installed in the surgical portion for fixing the surrounding skin and muscles in the surgical portion and disposed between the femur and the surrounding muscles and skin.

The tubular element 20 is disposed between the retractor 10 and the femur 404. According to one aspect of the present invention, the tubular element 20 is connected to the retractor 10 by a connecting means (not shown), thereby setting a certain gap between the tubular element 20 and the retractor 10. As for the shape of the tubular element 20, at least part of the tubular element 20 may be formed correspondingly to the surface shape of the retractor. In another embodiment, all parts of the tubular element may be formed correspondingly to the surface shape of the retractor.

Figure 7:
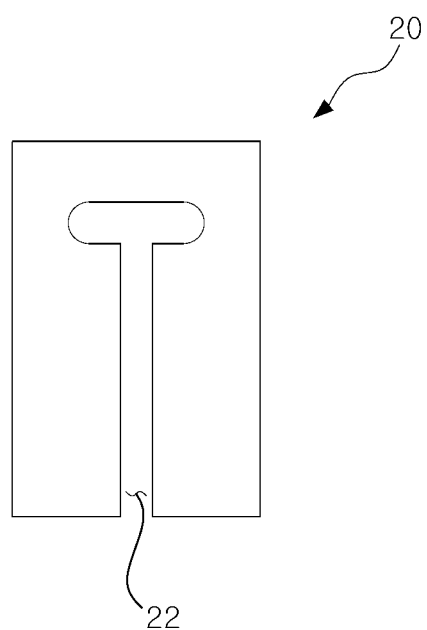
FIGS. 7 and 8 show a slit of a tubular element according to one embodiment of the present invention.
Figure 8:
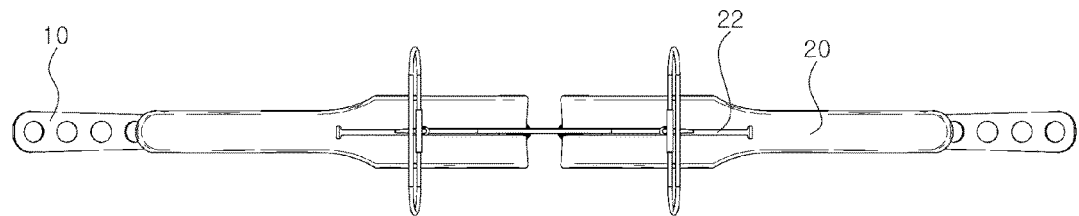

The gigli saw 30 is inserted along the certain space formed above as indicated by the arrow in FIG. 4. To guide the gigli saw 30 inserted between the retractor 10 and the tubular element 20 and resect the neck of the femur 404 and the capsules 402, a slit 22 may be formed on the surface of the tubular element 20 as shown in FIGS. 7 and 8. The slit 22 is formed to penetrate from one surface of the tubular element 20 to the other surface opposite to the one surface. Then the gigli saw 30 travels back and forth between the one surface side and the other surface side by passing through the slit 22, and the slit 22 guides the gigli saw 30 to perform resection of the neck.

In addition, according to another aspect, the tubular element 20 may be separately inserted between the retractor 10 and the femur 404 after the retractor 10 is inserted. That is, the retractor 10 and the tubular element 20 may not be connected by the connecting means. In this case, at least part of the tubular element 20 may be formed identically to the surface shape of the retractor 10. In another embodiment, all parts of the tubular elements may be formed identically to the surface shape of the retractor 10. Also, when the connecting means are not formed, the tubular element 20 may be prepared to follow the overall contours of the surface shape of the retractor 10. The tubular element 20 is disposed at an inner side of the retractor 10 and creates a gap between the tubular element 20 and the retractor 10 through which the gigli saw 30 passes when being in contact with the retractor 10. To this end, at least part of the tubular element 20 may be deformed, bent or curved. For instance, at least part of the tubular element 20 is formed to be curved laterally.

Figure 9:
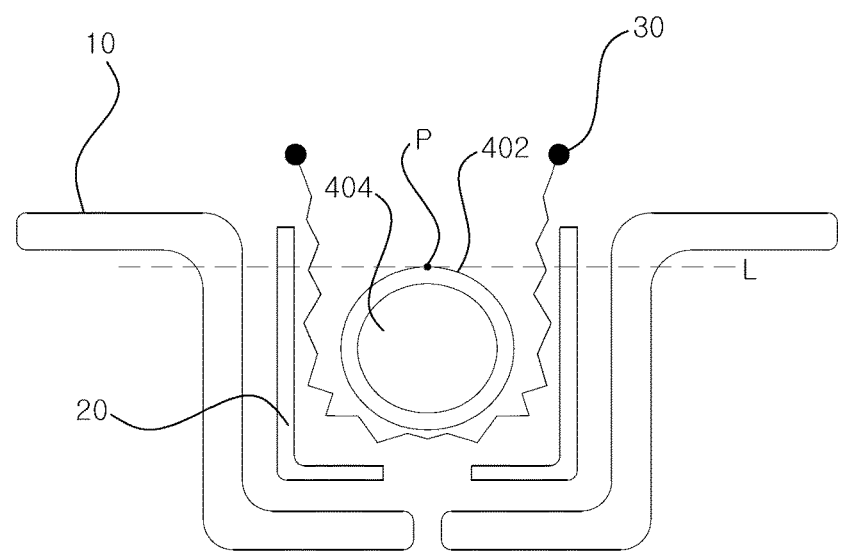
FIG. 9 shows a conceptualized view of a retractor having a tubular element according to one embodiment of the present invention.

Referring to FIG. 8, the slit 22 may extend in the longitudinal direction of the tubular element 20. The slit 22 may be formed in at least part of the surface in the longitudinal direction of the tubular element 20. Preferably, the slit 22 may be formed along the surface of the tubular element 20 to a line L formed by drawing a straight line from a point P in a circumferential surface of the femur 404 at a surgeon's side as shown in FIG. 9. The line L is where resection ends.

Figure 10:
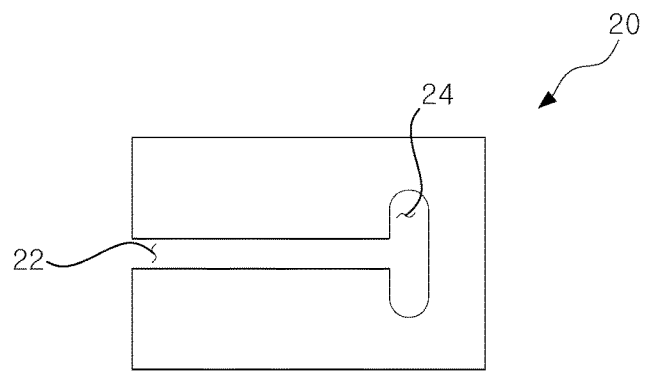
FIG. 10 shows a slit formed in the tubular element according to one embodiment of the present invention.
Figure 11:
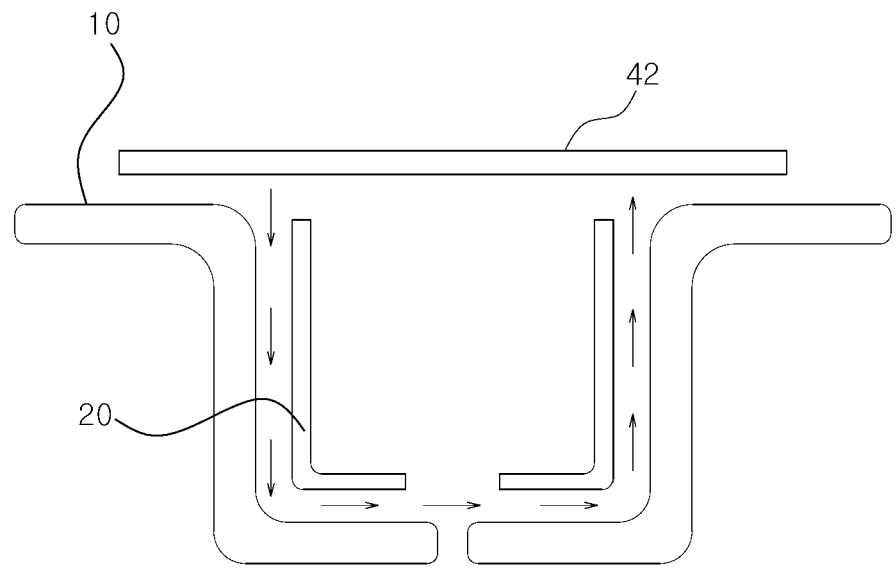
FIG. 11 shows a retractor according to another embodiment of the present invention.
Figure 12:
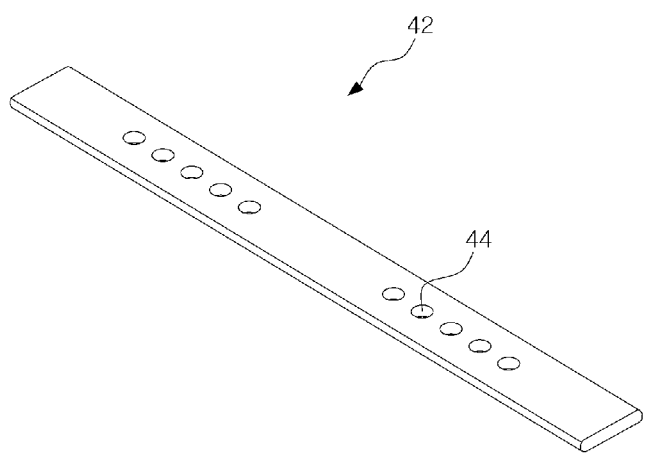
FIG. 12 shows a bar member being a fixing means for a retractor according to another embodiment of the present invention.

According to another embodiment of the present invention, both ends of the slit 22 may be formed differently from the shape of other parts of the slit 22. As shown in FIG. 10, both ends 24 of the slit 22 may be expanded compared to other parts of the slit 22. For example, the both ends 24 of the slit 22 may expand in a direction substantially perpendicular to the longitudinal direction of the slit 22. Also, the inner faces of the expanded both ends 24 of the slit 22 are rounded to facilitate the motion of the gigli saw.

According to the present invention, since resection using the gigli saw 30 can be done at a desirable location by the slit 22 of the tubular element 20, the gigli saw 30 is guided such that the resection of the capsules and the neck is accomplished at an exact location. Moreover, according to the present invention, bone resection and capsule release are made easy by using the gigli saw 30 correctly guided to the exact resection location, the neck can be resected at the exact position by not using a standard power saw, and inadvertently cutting greater trochanter is avoided. Also, the head is readily removed without cutting a second neck due to capsular release, and exposure of the femur and the acetabulum is excellent and capsule is easily repaired.

According to another embodiment of the present invention, the retractor 10 for fixing the skin and the muscle around the surgical portion may comprise a fixing means for lining up the retractor 10 such that the gigli saw 30 readily passes without the need of manpower when fixing the retractor 10. During the direct anterior approach surgery, surgical efficiency can be improved as required manpower decreases if two retractors are fixed by themselves.

Referring to FIGS. 11, 12, 13a and 13b, according to one aspect of the present invention, the fixing means for lining up the retractor 10 comprise a bar member 42. The cross section of the bar member 42 may be circular, rectangular, square, or polygonal and not be limited thereto. The cross section can take any shape if the bar member 42 is detachably coupled to the retractor 10 and fixes the retractor 10.

Figure 13A:
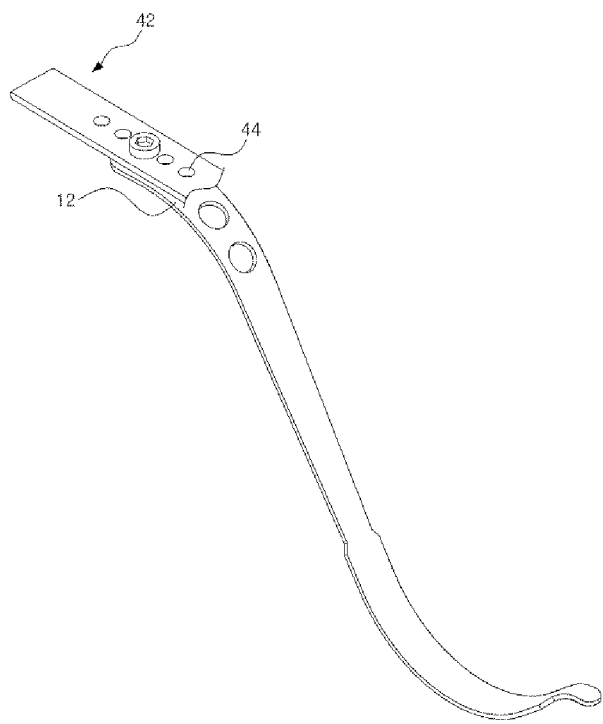
FIGS. 13a and 13b show a coupling of a retractor and a bar member according to another embodiment of the present invention.
Figure 13B:
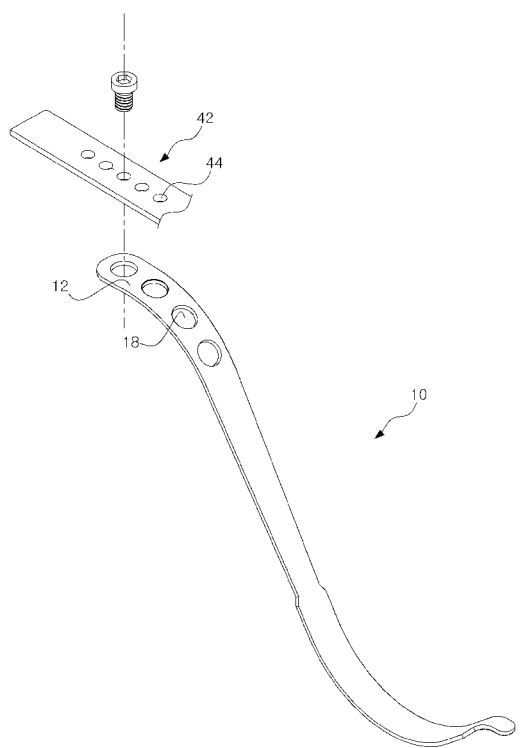

The bar member 42 is detachably installed in grip parts 12 of a pair of retractors 10 disposed to face with each other and helps the retractor be fixed without the aid of manpower when the retractors 10 are fixed in the surgical area. For installation, a plurality of mounting holes 44 may be formed for coupling with the retractors 10 in the bar member 42. Correspondingly, a plurality of coupling holes 18 are formed in the grip parts 12 of the retractors 10. Since several coupling holes 18 and the mounting holes 44 are formed, the coupling location of the mounting hole 44 and the coupling hole 18 can be changed dependent on the size of the surgical subject, thereby adjusting coupling length. For instance, the size of the coupling holes and the mounting holes may be formed identically, and a snap-fit pin may be used to fasten the coupling hole and the mounting hole. Also, as shown in FIGS. 13a and 13b, for instance, screw threads may be formed in the inner circumferential faces of the mounting hole 44 and the coupling hole 18 for screw connection. FIGS. 13a and 13b shows a coupling state of one side of the pair of the retractors, but the other side can be coupled by the same method.

In addition, according to another aspect of the present invention, the fixing means for lining up the retractor may be a magnet. Regions of the retractors, which are inserted into the surgical portion, are magnetized to have different polarities, respectively, thereby lining up the retractors without the aid of manpower.

According to another embodiment of the present invention, the retractor 10 for fixing the skin and the muscles around the surgical portion may comprise a protective means capable of minimizing damage to the surrounding muscles which may occur by the use of the retractor 10. As described above, muscle damage frequently occurs especially for a muscular patient. Specifically, as prior retractors are narrow and have cornered or sharp parts, the retractors tend to place high force on a small area of the muscle and pull the muscle in direct contact, thereby causing muscle damage. To prevent such problems, the protective means according to the present invention comprises a rounded part 14 or a shield 16 for a retractor.

Figure 14:
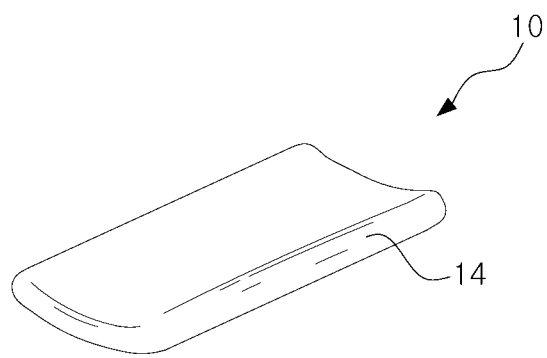
FIG. 14 shows a retractor including a protective means according to still another embodiment of the present invention.

As shown in FIG. 14, the protective means of the retractor for preventing muscle damage according to an aspect of the present invention may comprise a rounded part 14. FIG. 14 only shows a part of the retractors where the contact area between the retractor 10 and the muscle is the widest. The rounded part 14, as shown in FIG. 14, may be included in the overall shape of the retractor 10 or the part of the retractor 10 where the contact area is the widest is configured to include the rounded part 14. The rounded part 14 is formed with unsharp and smoothly curved surfaces compared to the cornered edges of the prior retractors. As a result, damage to the muscles in contact is minimized and stress applied on soft tissues is reduced.

Figure 15:
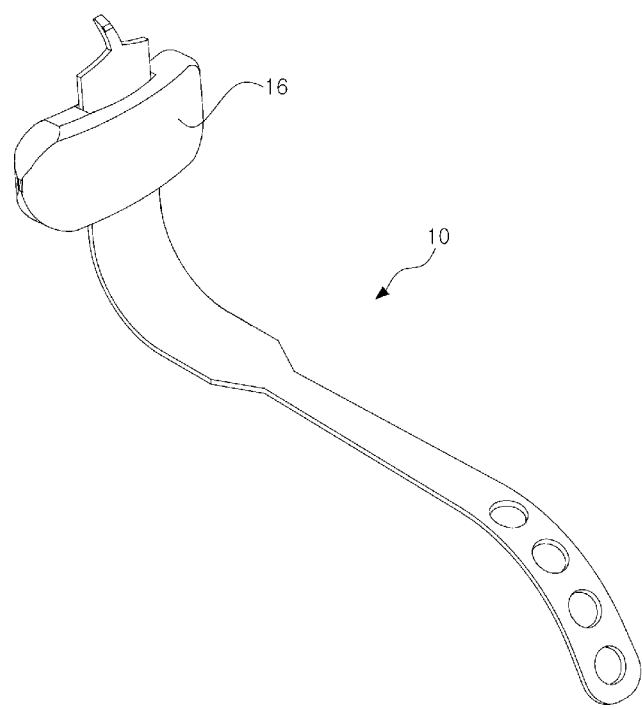
FIG. 15 shows a retractor including a protective means according to still another embodiment of the present invention.

In addition, referring to FIG. 15, the protective means of the retractor for preventing muscle damage according to another aspect of the present invention comprises a shield 16. The shield is configured to adjust its position with respect to the retractor 10 such that the shield 16 is provided in the area where most contact with the muscles occurs. In other words, the shield 16 is movably fixed on the retractor 10. The shield 16 can be immediately moved to an area where the muscles need to be protected, which continuously changes as operation proceeds.

The shape of the shield 16 can be any shape as far as the shield takes the shape of laterally expanding from the narrow retractor. Also, the edges of the shield 16 are rounded for preventing muscle damage when being in contact with the muscle.

Figure 16:
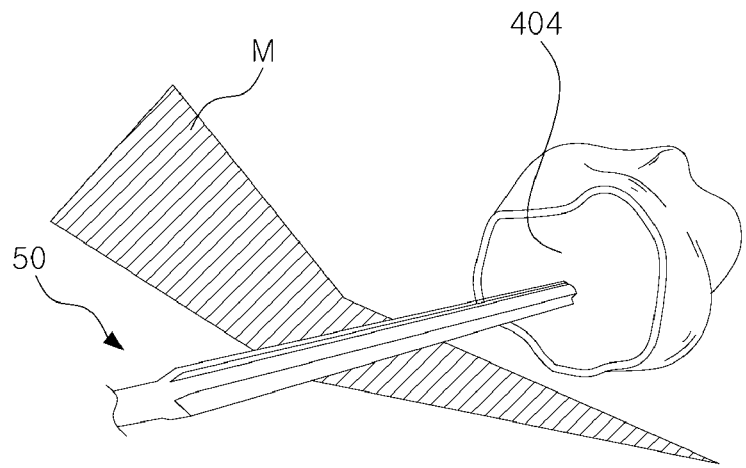
FIG. 16 shows a reamer in use in a femur.

Below a starter reamer according to the present invention is described. As shown in FIG. 16, a starter reamer 50 used for enlarging a femoral stem may cause damage to the surrounding muscles M as the starter reamer 50 advances. Accordingly, to resolve such issue, the reamer 50 according to the present invention comprises at least one of a telescopic protector 60 for preventing damage to the surrounding muscles M and a flexible shaft 54.

Figure 17:
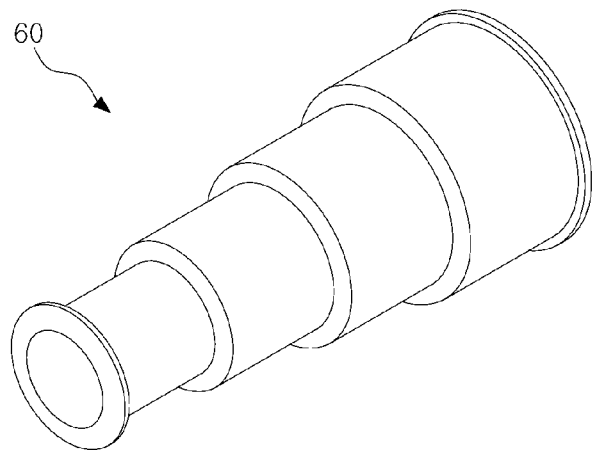
FIG. 17 shows a perspective view of a telescopic protector according to still another embodiment of the present invention.
Figure 18:
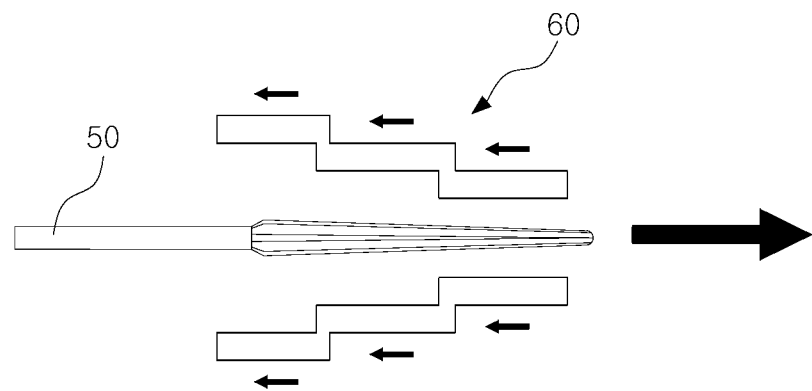
FIG. 18 is a conceptualized view of the telescopic protector in use of FIG. 17.

As shown in FIGS. 17 and 18, according to one embodiment of the present invention, the reamer may comprise a telescopic protector 60 disposed to surround the outer circumference of the reamer. The telescopic protector 60 may be a multistage cylinder with penetration holes. That is, the telescopic protector 60 may be a form of cannula capable of lengthening or shortening in the longitudinal direction. More specifically, the telescopic protector 60 comprises a plurality of cylinders, each of which has different diameter. Penetration holes are formed in each cylinder of the plurality of the cylinders, and the plurality of the cylinders are formed multistage.

Figure 19:
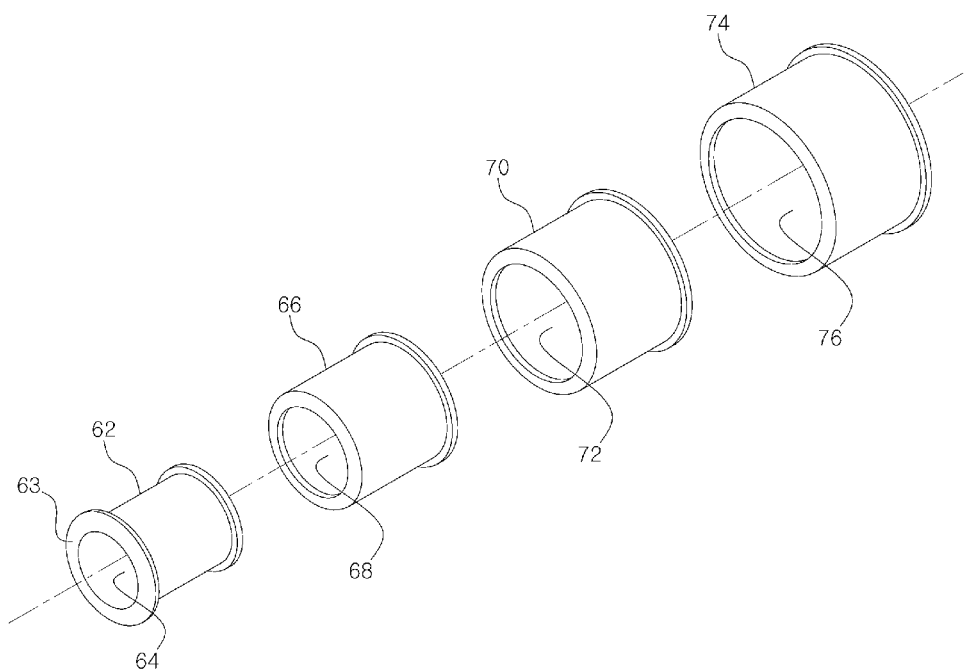
FIG. 19 is an exploded perspective view of the telescopic protector in FIG. 17.

Referring to FIG. 19, the telescopic protector 60 comprises a first rod 62 of a cylinder type, disposed at the most front location in a path of movement of the reamer 40. A first penetration hole 64 is formed to penetrate the longitudinal direction of the first rod 62. At the rear side of the first rod 62, a second rod 66 is installed. The second rod 66 is formed as a cylinder-type, like the first rod 62, and includes a second penetration hole 68 which penetrates the longitudinal direction of the second rod 66. The external diameter of the first rod 62 and the internal diameter of the second rod 66 are substantially identical or the internal diameter of the second rod 66 is formed larger, thereby inserting the first rod 62 into the second rod 66 if the second rod 66 slidably moves toward the first rod 62.

In addition, a third rod 70 is installed at the rear side of the second rod 66. The third rod 70 is formed as a cylinder and includes a third penetration hole 72 which penetrates the longitudinal direction of the third rod 70. The external diameter of the second rod 66 and the internal diameter of the third rod 70 are substantially identical or the internal diameter of the third rod 70 is formed larger. Accordingly, when the third rod 70 slidably moves toward the second rod 66, the second rod 66 is received inside the third rod 70.

Moreover, a fourth rod 74 is installed at the rear side of the third rod 70. The fourth rod 74 is formed as a cylinder and includes a fourth penetration hole 76 which penetrates the longitudinal direction of the fourth rod 74. The external diameter of the third rod 70 and the internal diameter of the fourth rod 74 are substantially identical or the internal diameter of the fourth rod 74 is formed larger. Accordingly, when the fourth rod 74 slidably moves toward the third rod 70, the third rod 70 is received inside the fourth rod 74.

As a result, when the first to fourth rods (62, 66, 70, 74) collapses, the fourth rod 74 is disposed outermost, the third rod 70 is disposed inside the fourth rod 75, the second rod 66 is disposed inside the third rod 70, the first rod 62 is disposed inside the second rod 66, and only the fourth rod 74 is observable from the outside.

When the first to fourth rods (62, 66, 70, 74) are all collapsed, a protruded portion 63 protruding radially from the outer circumferential surface of the front part of the first rod 62 to prevent separation. The protruded portion 63 protrudes radially from the inner circumference of the first rod 62 and protrudes further than the inner diameter of the second rod 66, thereby preventing separation of the first to fourth rods (62, 66, 70, 74).

In the drawings, only four cylinders are drawn. However, more or less cylinders may used by the above-described method.

The reamer 50, as shown in FIG. 18, is disposed inside the telescopic protector 60. The protector for the starter reamer 50 is formed as cannula and lengthens or shortens itself like an antenna. The telescopic protector 60 prevents the sharp parts of the reamer from contacting the surrounding muscles until the starter reamer 50 reaches the femur to enlarge a hole for the femoral stem during surgery, thereby preventing muscle damage by the starter reamer.

Figure 20:
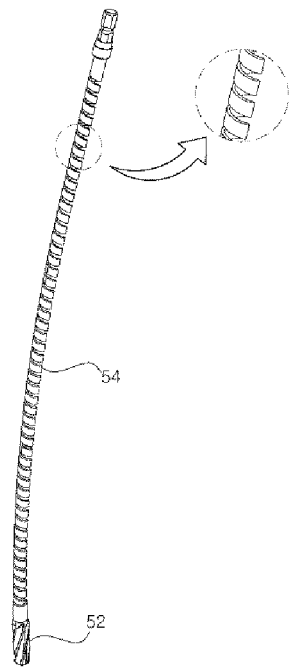
FIGS. 20 and 21 show a reamer including a flexible shaft according to still another embodiment of the present invention.
Figure 21:
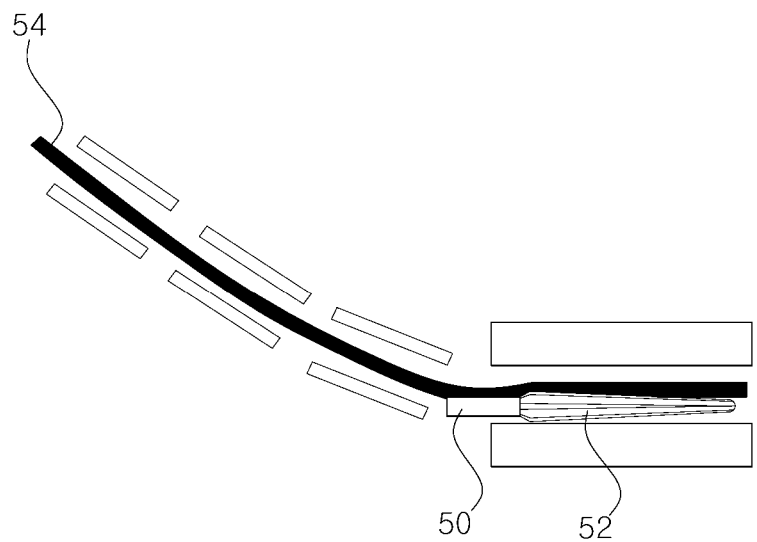

According to another embodiment of the present invention, the reamer 50 may comprise a flexible shaft 54 to prevent damage to the surrounding muscles. As shown in FIGS. 20 and 21, the reamer 50 comprises a cutting portion 52 disposed at a front side in the direction along which the reamer advances and having cutting edges on the outer circumference and a shaft 54 disposed at a rear side of the cutting portion 52 and connected to the cutting portion 52. Since the flexible shaft 54 is formed by a wire of a flexible material, unlike prior starter reamers, it is unlikely to cause damage to the muscles when coming in contact with the muscles, and muscle damage can be prevented through manipulating angles of the flexible shaft.

According to the present invention, the set of surgical instruments for an artificial hip joint implant comprises a broach having a modular broach. The broach is a tool used to prepare a predefined space for the implant by enlarging the hole formed by the reamer for seating the femoral stem in the femur. The length of currently used standard broaches brings a possibility of causing damage to the muscle. The part of the broach inside the bone does not result in muscle damage, but the part of the broach placed outside the bone, which contacts with the muscle, can damage the muscles as the broach advances. To solve such problem, the broach 80 according to the present invention may comprise a modular broach having a plurality of cutting segments.

Figure 22:
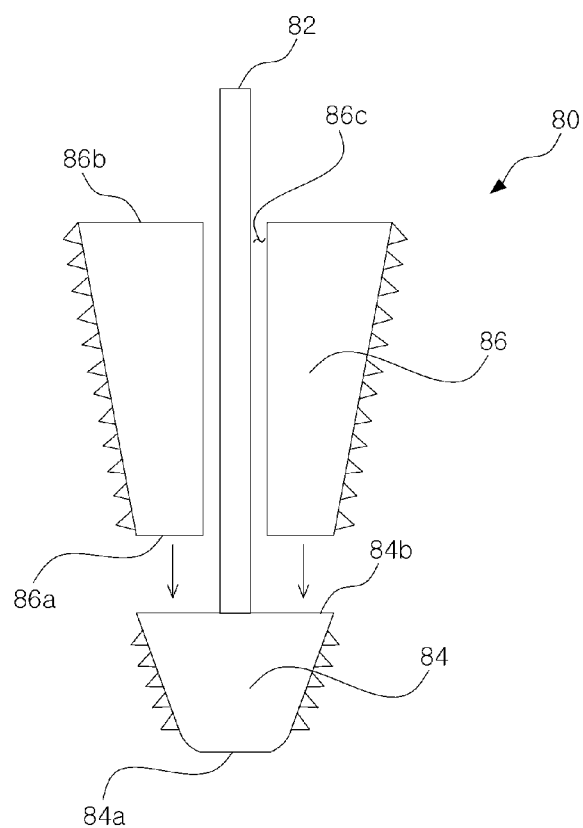
FIG. 22 shows a broach including a modular broach according to still another embodiment of the present invention.
Figure 23:
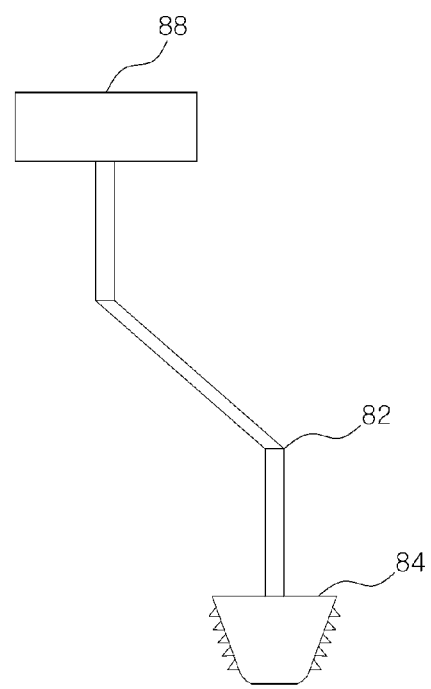
FIG. 23 shows a broach including a modular broach according to still another embodiment of the present invention.

FIG. 22 illustrates the broach 80 comprising a modular broach according to one embodiment of the present invention. According to the present embodiment, the modular broach comprises a guide member 82, a first cutting segment 84, and a second cutting segment 86.

The first cutting segment 84 being a broach element first placed inside the femoral stem is configured to have a shorter length than a common broach. On the outer circumference of the first cutting segment 84, cutting edges for enlarging and trimming a hole for stem insertion are formed. The cross sections of the first cutting segment 84 may differ in a way that the cross section at one end 84*a* around tip portion may be created smaller than that at the other end 84*b*. Preferably, the first cutting segment 84 is wedge-shaped to facilitate insertion for enlarging the hole.

The guide member 82 is coupled to the first cutting segment 84. Preferably, the first cutting segment 84 may be detachably coupled to one end of the guide member 82. The guide member 82 may be a rod for lining up the first cutting segment 84 and the second cutting segment 86. The cross section of the guide member 82 can take any shape, such as a polygon including a circle, an ellipse, and a rectangle, but preferably a rod with a square cross section such that rotation of the broach around the guide member is well prevented.

In addition, the guide member 82 may be configured to have a bent shape to stay away from surrounding tissues. For instance, the guide member 82 can be an offset type as a strike portion 88 and the broach segment are offset with each other. In case of prior offset broach handles, when an impaction force is applied the impaction force is partially converted into a second vector. As a result, inadequate femur preparation with poor initial stability of implant or inadvertent femur fracture happens. On the other hand, in the broach according to the present invention, as the guide member is made offset, the offset handle causing the aforementioned problem is not needed.

Also, the modular broach according to the present invention comprises the second cutting segment 86. The first cutting segment connected to the guide member 82 is placed in the femoral canal, and the second cutting segment 86 is inserted from the rear side of the first cutting segment 84. The second cutting segment has a penetration hole which penetrates in its longitudinal direction around the center.

The second cutting segment 86 has cutting edges on the outer circumference, and the cross sections of the second cutting segment 86 along the longitudinal direction may be formed differently such that the cross section at one end 86*a* around tip portion may be created smaller than that at the other end 86*b*. Preferably, the outer circumference of the second cutting segment 86 at the one end 86*a* and the outer circumference of the first cutting segment 84 at the other end 84*b* may be formed substantially the same. In such case, the second cutting segment 86 is in the form of a circular truncated cone with increasing cross sections along the longitudinal direction. The second cutting segment 86 is fit in the guide member 82 provided with the first cutting segment 84 and, thus, provides an effect of extending the first cutting segment 84. According to the broach of the present invention, a broach commonly formed as one body is divided into a plurality of broach segments, and the segments are seated in the femoral stem one by one. This makes the broach of the present invention function as the common broach since the size of the broach becomes the same with that of the broach formed as one body. Moreover, damage to the surroundings are avoided since most of the broach segments are placed inside the femoral canal as additional cutting segments are inserted after canal preparation by one cutting segment is finished.

Also, additional third, fourth cutting segments and so on may be included to be placed inside the femoral canal through the guide member based on need by using the aforementioned method. As each segment is prepared by dividing the prior lengthy broach into small pieces, the each segment is to have a shorter length compared to the prior broach. Since one segment is inserted in the bone and additional segments are subsequently inserted when necessary, muscle damage is fundamentally prevented.

Figure 24A:
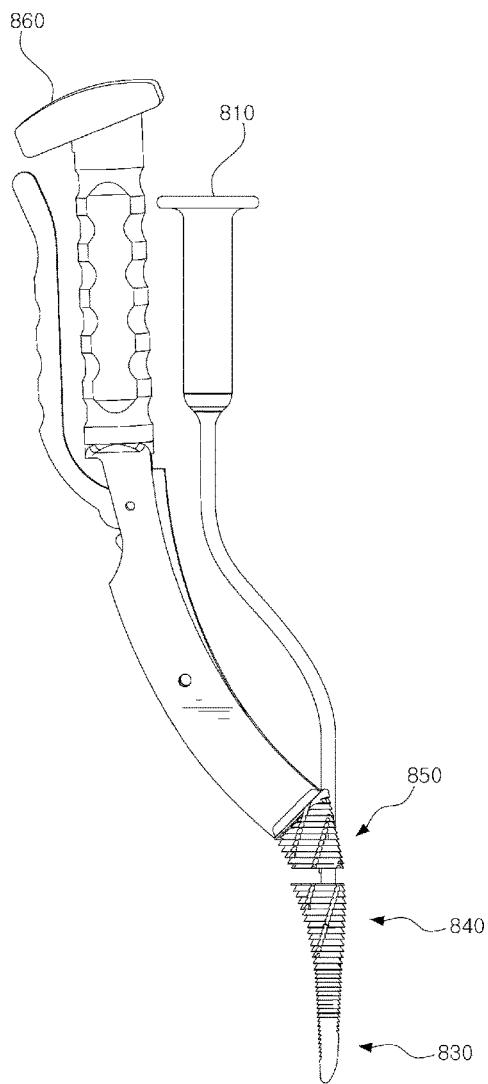
FIGS. 24a and 24b show a broach including a modular broach according to still another embodiment of the present invention.
Figure 24B:
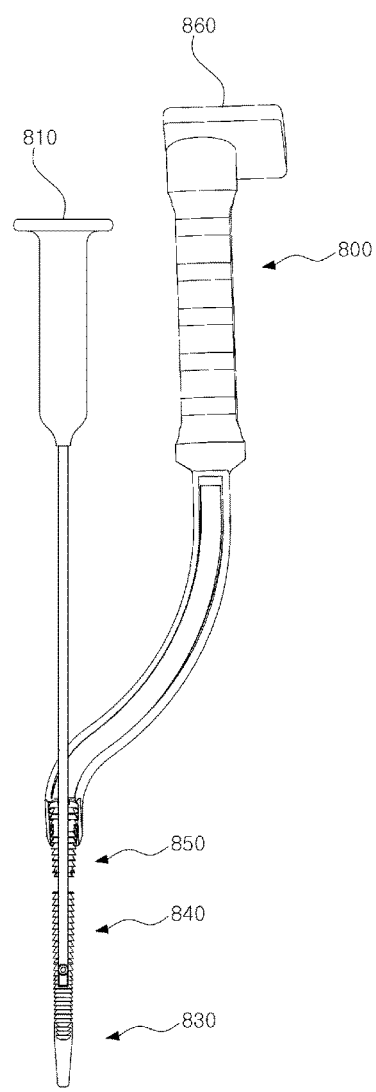

FIGS. 24*a* and 24*b* show a broach 800 comprising a modular broach according to another embodiment of the present invention. According to the present invention, the broach 800 comprises a guide member 810, a modular broach, and a broach handle 860, and the modular broach comprises a plurality cutting segments (830, 840, 850). The present embodiment shows a broach having three cutting segments, but a greater or fewer number of cutting segments may be provided.

Figure 25:
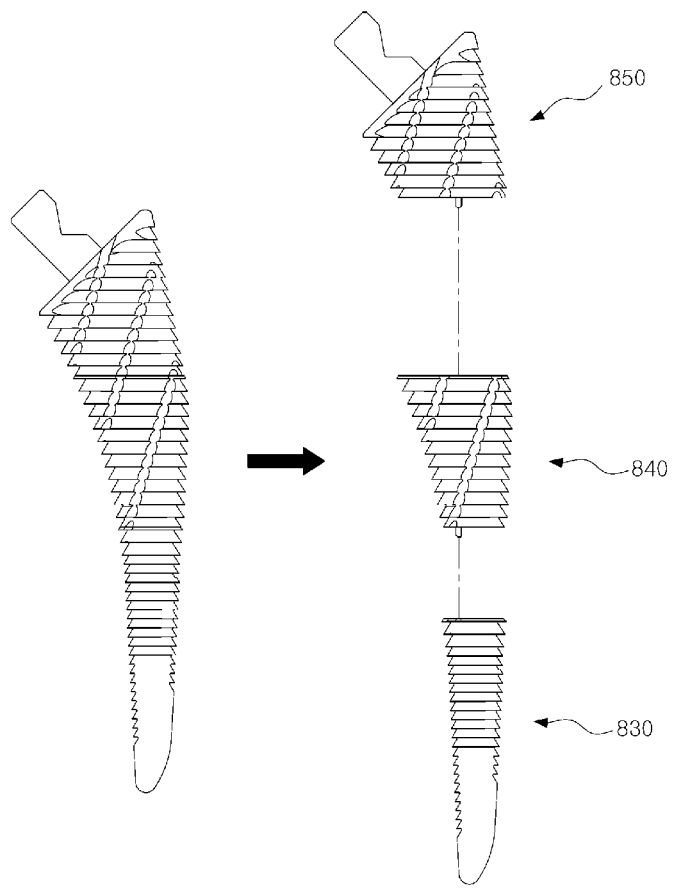
FIG. 25 shows a modular broach according to still another embodiment of the present invention.

As shown in FIG. 25, the modular broach according to the present invention comprises a plurality of cutting segments, and the plurality of the cutting segments includes: a first cutting segment 830; a second cutting segment 840 coupled to a top of the first cutting segment 830; and a third cutting segment 850, one side of which is coupled to a top of the second cutting segment 840 and the other side of which is coupled to the broach handle 860.

Figure 26A:
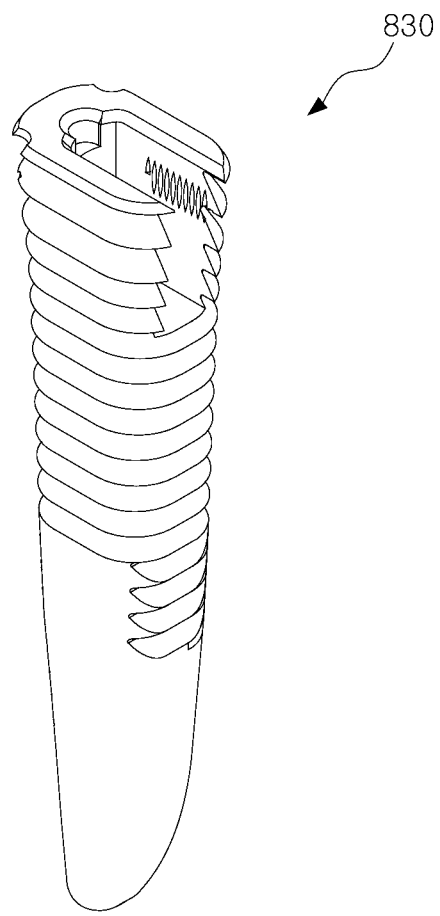
FIGS. 26a to 26c show a perspective view, a top view and a side view of a first cutting segment of a modular broach, respectively.
Figure 26B:
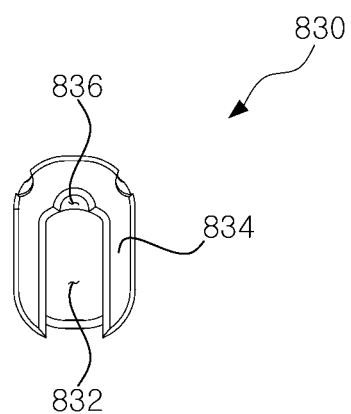
Figure 26C:
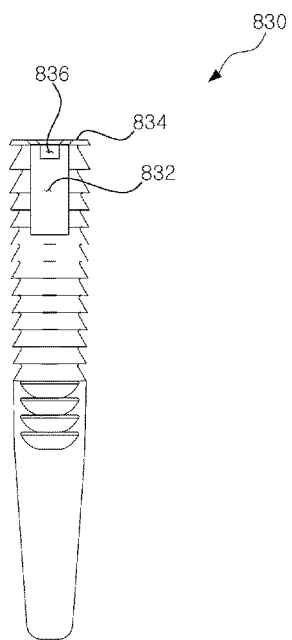

As shown in FIGS. 26*a* to 26*c*, the first cutting segment 830 takes a shape of increasing cross sections from a tip side to a distal side and is provided with cutting edges on the outer circumference. Also, an upper face 834 of the first cutting segment 830 is configured to be planar for easy coupling with the second cutting segments 840.

At the upper side of the first cutting segment 830, a first cutout portion 832 where part of the volume is removed to receive the guide member 810, which will be described below. Also, a protrusion receiving portion 836 is formed in a part of the surface of the first cutting segment 830 with which the first cutout portion 832 contacts. The protrusion receiving portion 836 is formed by being depressed further toward the first cutting segment 830. The protrusion receiving portion 836, as will be described later, guides an exact position when being coupled to the second cutting segment 840.

Figure 27A:
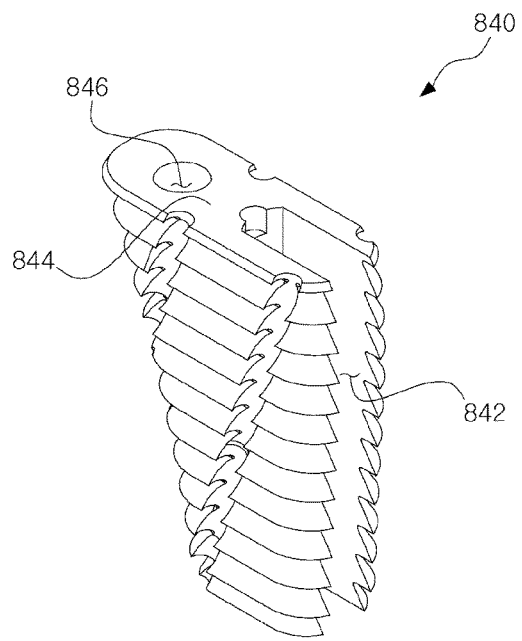
FIGS. 27a to 27c show a perspective view, a top view and a side view of a second cutting segment of a modular broach, respectively.
Figure 27B:
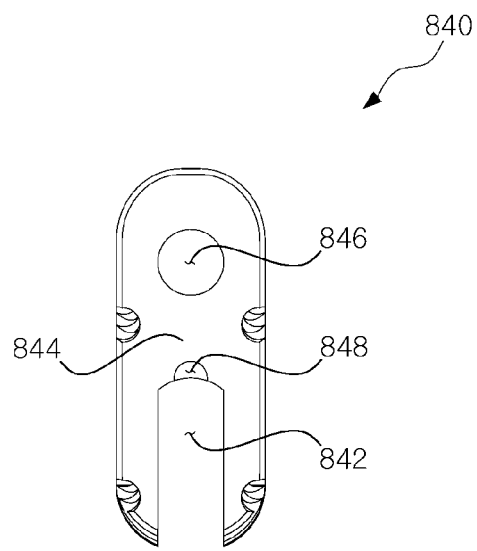
Figure 27C:
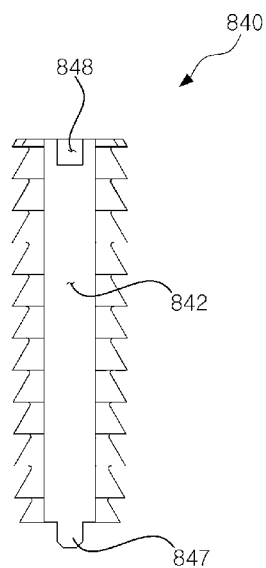

Referring to FIGS. 27a to 27c, the second cutting segment 840 takes the shape of increasing cross sections from the lower part to the upper part and has cutting edges on the outer circumference. Moreover, an upper face 844 of the second cutting segment 840 is formed to be planar for easy coupling with the third cutting segment 850 coupled to the upper side of the second cutting segment 840. The lower face of the second cutting segment 840 is formed to be planar for easy coupling with the upper face 834 of the first cutting segment 830.

A second cutout portion 842 in which a part of the volume is removed from the second cutting segment 840 to receive the guide member 810 at the upper side of the second cutting segment 840. Also, a protrusion receiving portion 848 is formed in a part of the surface of the second cutting segment 840 with which the second cutout portion 842 contacts. The protrusion receiving portion 848 is formed to be depressed further toward the second cutting segment 840. The protrusion receiving portion 848 guides the third cutting segment 850 to be received in a correct position when being coupled to the third cutting segment 850. Also, at the other side of the second cutout portion 842 provided is a hole 846 to which an auxiliary guide member 820 is coupled.

At the lower part of the second cutting segment 840, a protrusion 847 is formed, which protrudes downward. The protrusion 847 is inserted in the protrusion receiving portion 836 formed in the first cutting segment 830 and guides the first cutting segment 830 to be correctly connected to the second cutting segment 840, which will be described in more detail below with the coupling of the second cutting segment 840 and the third cutting segment 850.

Figure 28A:
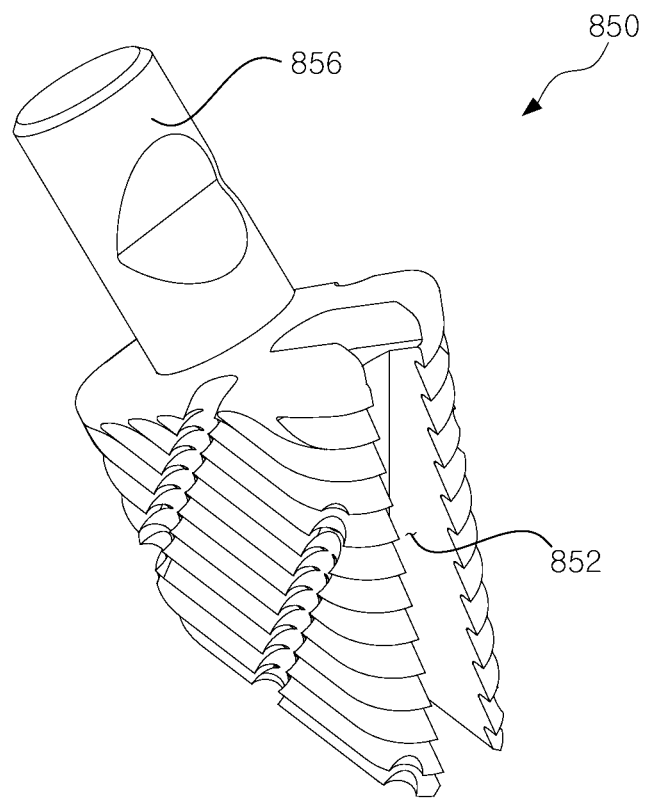
FIGS. 28a to 28c show a perspective view, a top view and a side view of a third cutting segment of a modular broach, respectively.
Figure 28B:
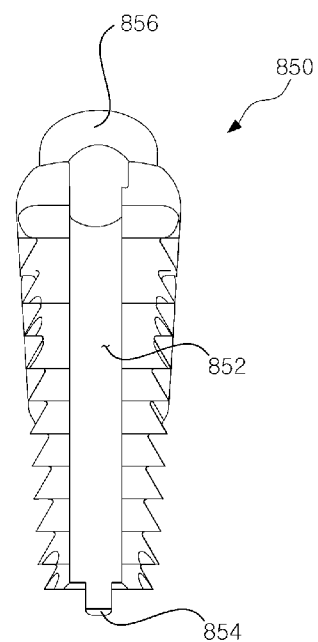
Figure 28C:
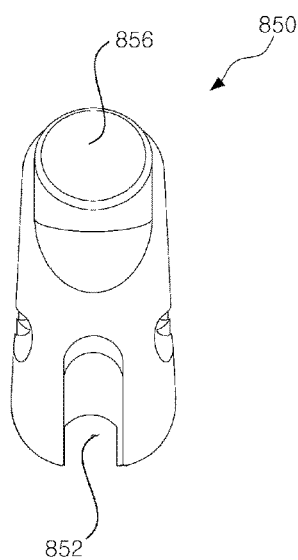

As shown in FIGS. 28a to 28c, the third cutting segment 850 takes the shape of increasing cross sections from the lower part to the upper part and has cutting edges on the outer circumference.

An upper face of the third cutting segment 850 is inclined with respect to a horizontal direction and coupled to the broach handle 860. To this end, a fitting portion 856 fitting in the broach handle 860 is protruded obliquely from the upper face of the third cutting segment 850.

At the upper side of the third cutting segment 850, a third cutout portion 852 in which some volume of the third cutting segment 850 is removed to receive the guide member 810. At the lower side of the third cutting segment 850, a protrusion 854 protruding downward is formed. The protrusion 865 is inserted in the protrusion receiving portion 848 formed in the cutting segment 840 described above and guides the second cutting segment 840 to be correctly connected to the third cutting segment 850, which will be described below in more detail with the coupling of the first cutting segment 830 and the second cutting segment 840.

Figure 29:
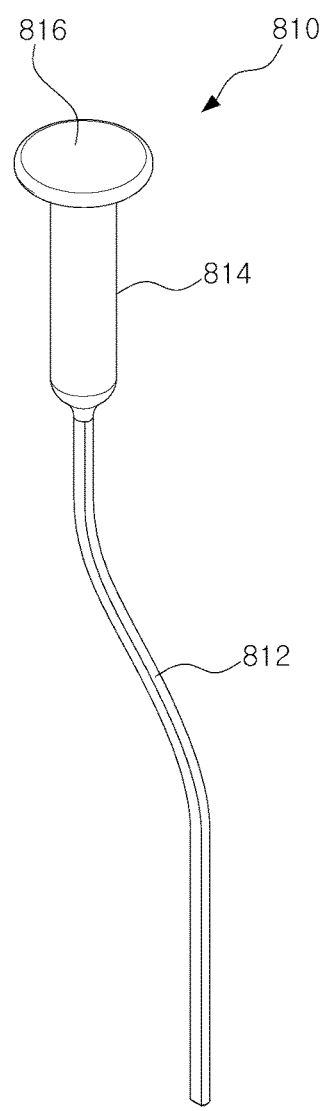
FIG. 29 shows a guide member of a broach according to the present invention.

FIG. 29 illustrates the guide member 810 according to the present invention. The first to third cutting segments (830, 840, 850) are provided in the guide member 810. The guide member 810 includes a shaft portion 812 having a bent shape to stay away from the surrounding tissues; and a grip part 814 including a strike portion 816 formed at an upper side of the shaft portion 812 for inserting the cutting segments by strike.

Figure 30A:
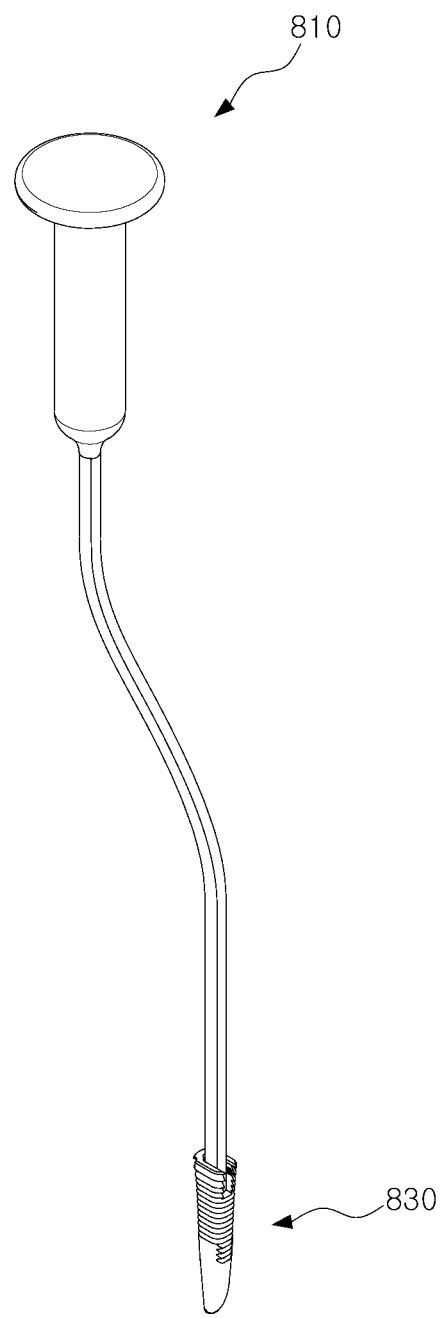
FIGS. 30a to 30c show a coupling state of a guide member and a first cutting segment according to the broach of the present invention.

As shown in FIG. 30a, the first cutting segment 830 is coupled to the guide member 810. More specifically, one end of the shaft portion 812 of the guide member 810 is coupled to the first cutting segment 830. The first cutout portion 832 of the first cutting segment 830 is coupled to the shaft portion 812 by surface contact. The shape of the outer circumference of the shaft portion 812 is formed identically to the shape of the first cutout portion 832 to be easily fixed. Preferably, at least part of the outer circumference of the shaft portion 812 includes a horizontal profile and at least part of the first cutout portion 832 includes a horizontal profile to prevent rotation due to the horizontal geometry when the shaft portion 812 and the first cutout portion 832 are coupled to each other.

Figure 30B:
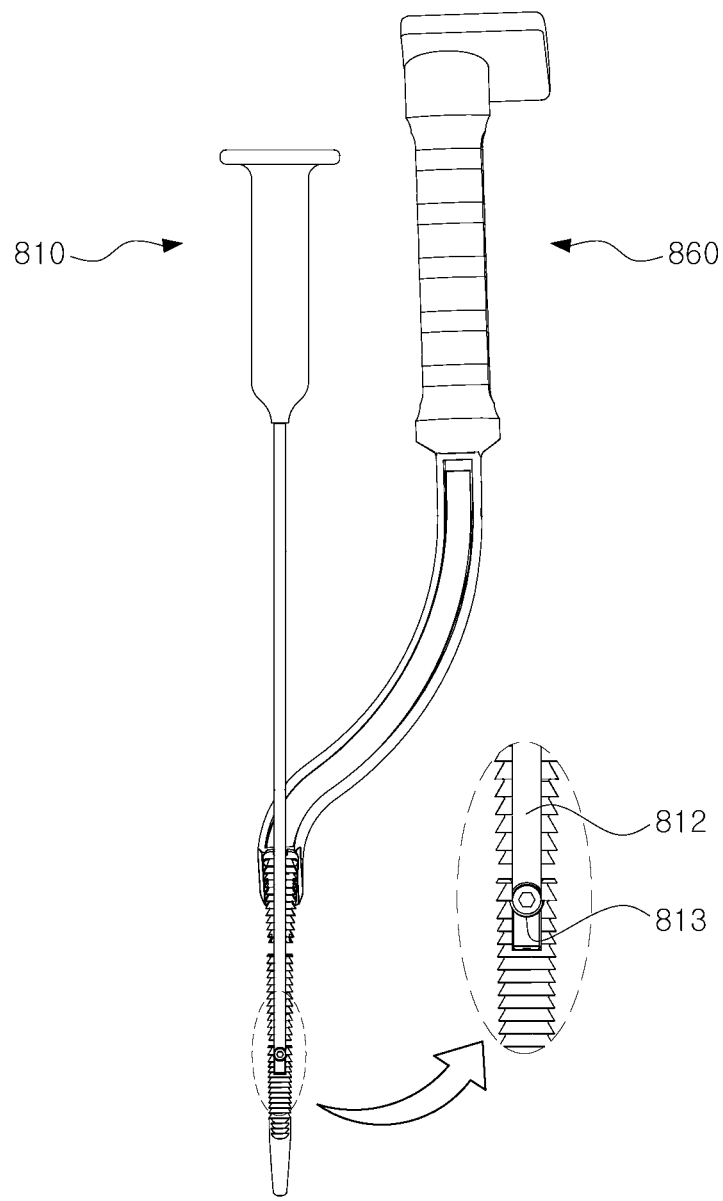
Figure 30C:
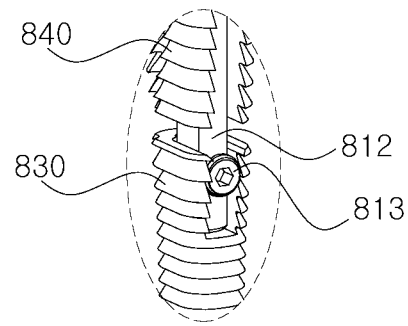

In addition, as the first cutting segment 830 corresponds to the modular broach which is first inserted in the femur, the first cutting segment 830 must be firmly fixed to the guide member 810 for exactly determining the position where the enlargement of hole starts. To this end, as shown in FIGS. 30b and 30c, screw connection may be employed for firm fixing of the guide member 810 and the first cutting segment 830. The screw may be a blot screw. The screw 813 is inserted at the first cutout portion 832 and penetrates the shaft portion 812. The penetrated screw 813 reaches a solid volume of the first cutting segment 830. The screw 813 is configured to penetrate at least part of the solid volume while not interfering with the cutting edges of the first cutting segment 830.

Figure 31A:
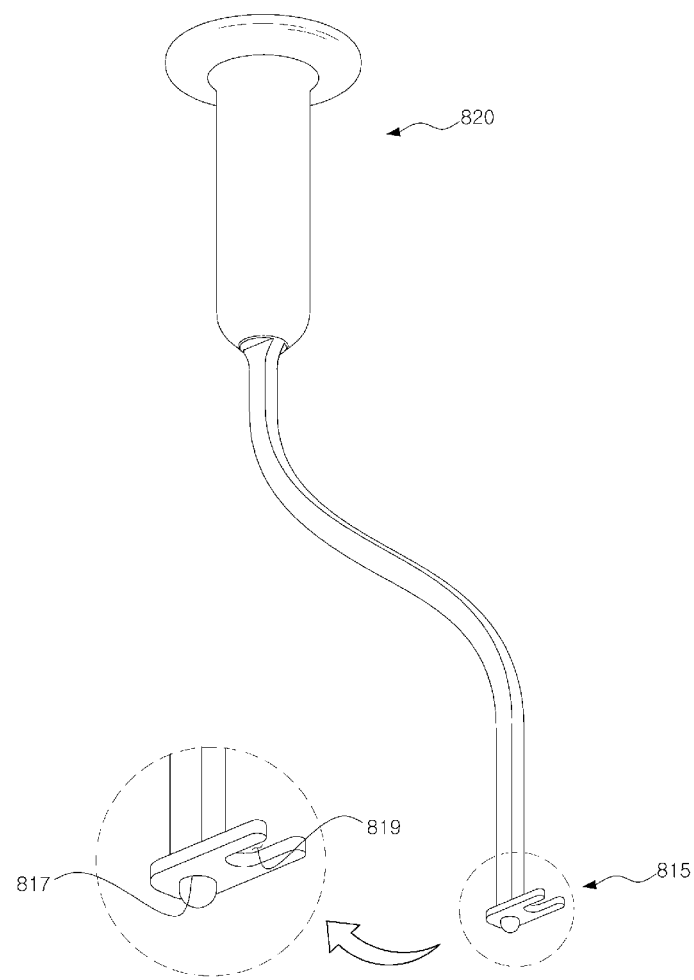
FIGS. 31a and 31b show an auxiliary guide member and a coupling member of the broach according to the present invention.
Figure 31B:
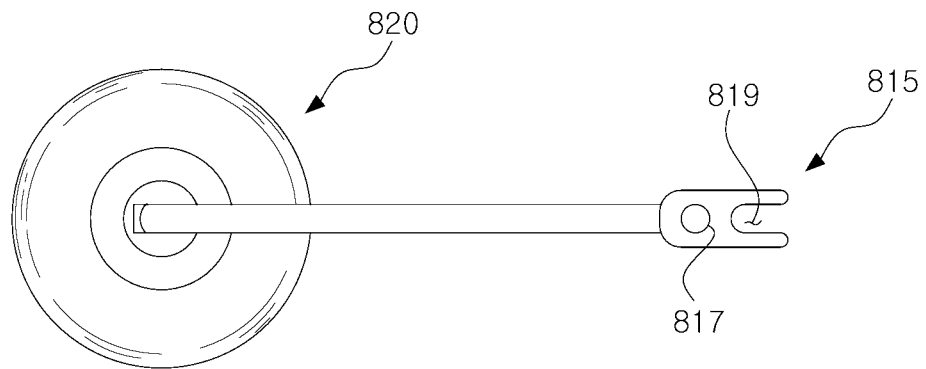
Figure 31C:
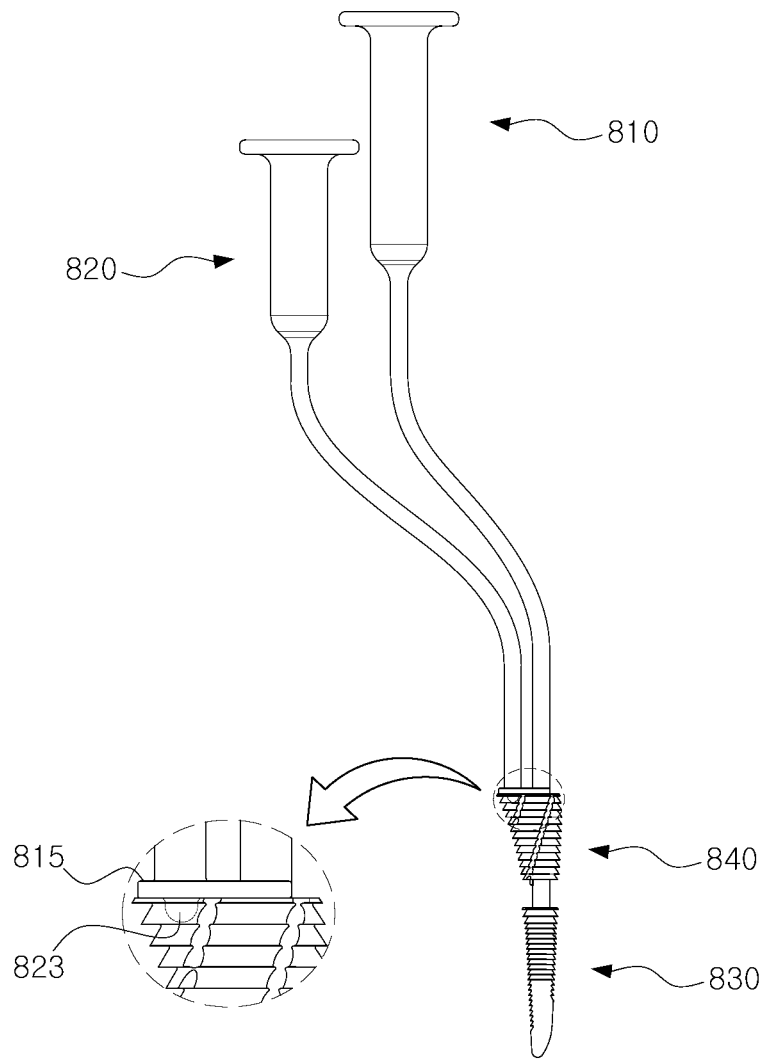
FIGS. 31c and 31d show a coupling state of a first cutting segment and a second cutting segment.
Figure 31D:
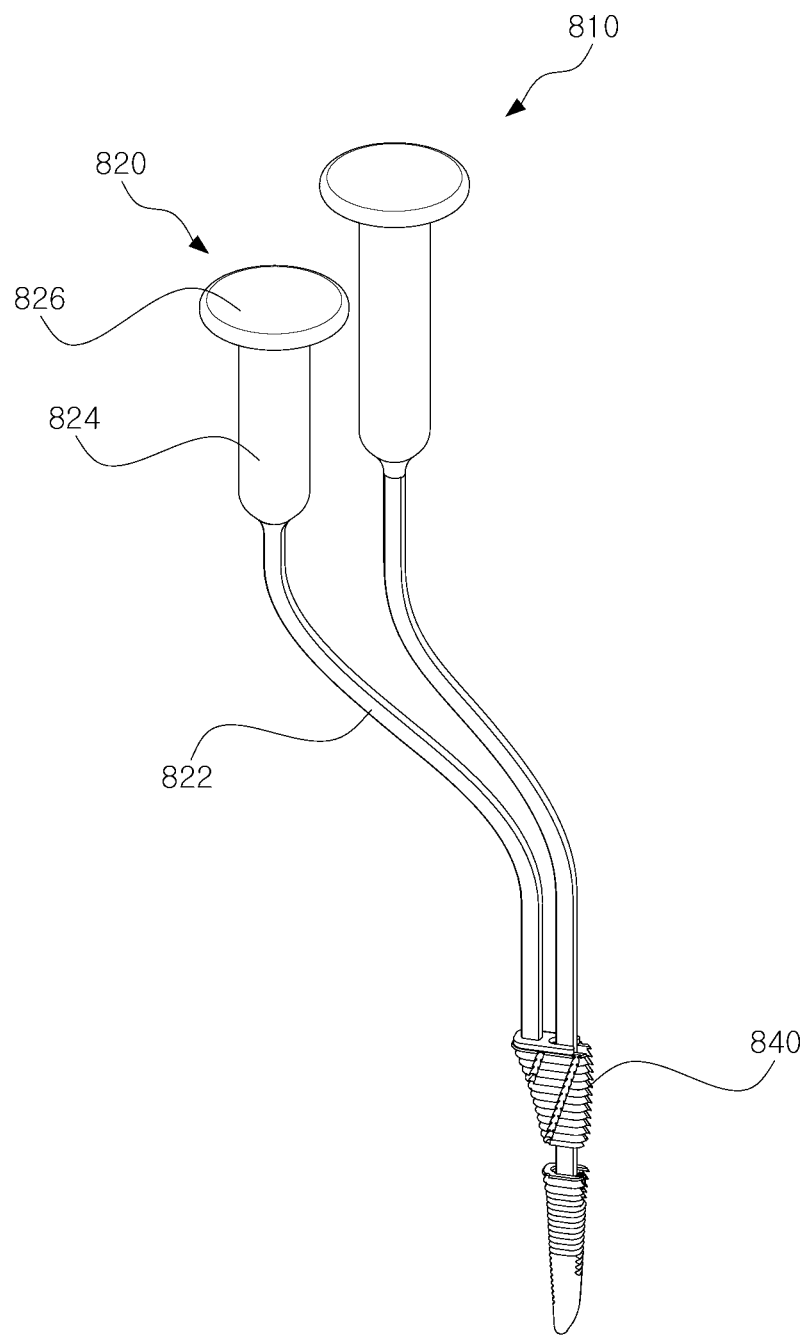

As shown in FIGS. 31a to 31b, an additional auxiliary guide member 820 may be provided to insert the second cutting segment 840. The auxiliary guide member 820 is used for providing impaction force to insert the second cutting segment 840. The auxiliary guide member 820 comprises a shaft portion 822 having a bent shape, like the guide member 810 and a grip portion 824 including a strike part 826 for inserting the second cutting segment 840 by striking. Referring to FIG. 31c, an end 823 of the shaft portion 822 takes a hemispheric shape such that force is uniformly distributed. The end 823 of the hemispheric shape is inserted in the hole 846 of the second cutting segment 840, as described above, for even distribution of force at the time of impacting.

Additionally, the auxiliary guide member 820 includes a coupling member 815 for coupling with the guide member 810 and the coupling member 815 is disposed at an upper side of the second cutting segment 840. The coupling member 815 includes an insertion hole 817 formed at one side for inserting the auxiliary guide member 820 and a slot 819 for mounting the guide member 810. The slot 819 has one side open such that the shaft portion 812 of the guide member 801 is fit by sliding surface contact.

Figure 32:
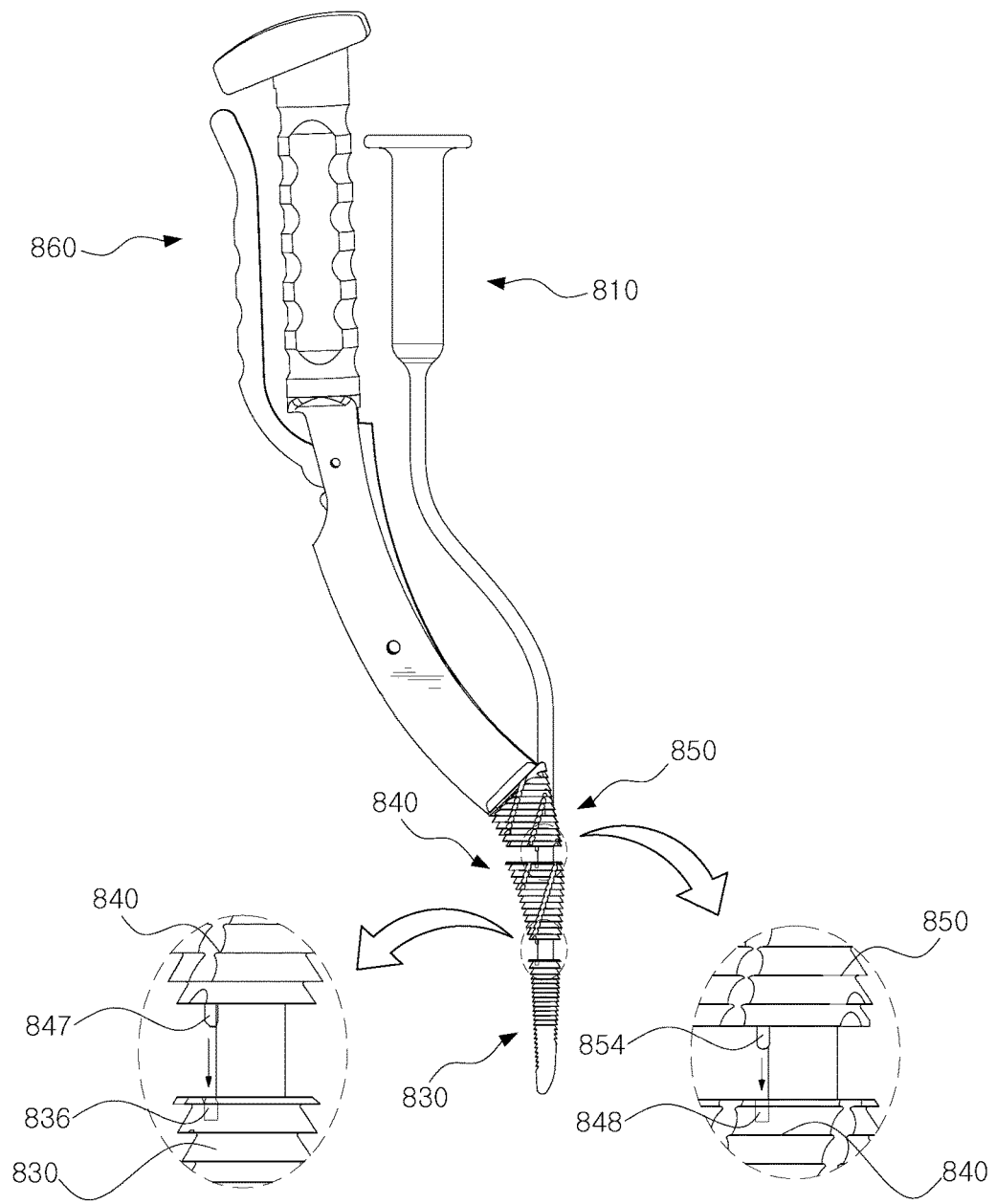
FIGS. 32 and 33 show a coupling state of each cutting segment.
Figure 33:
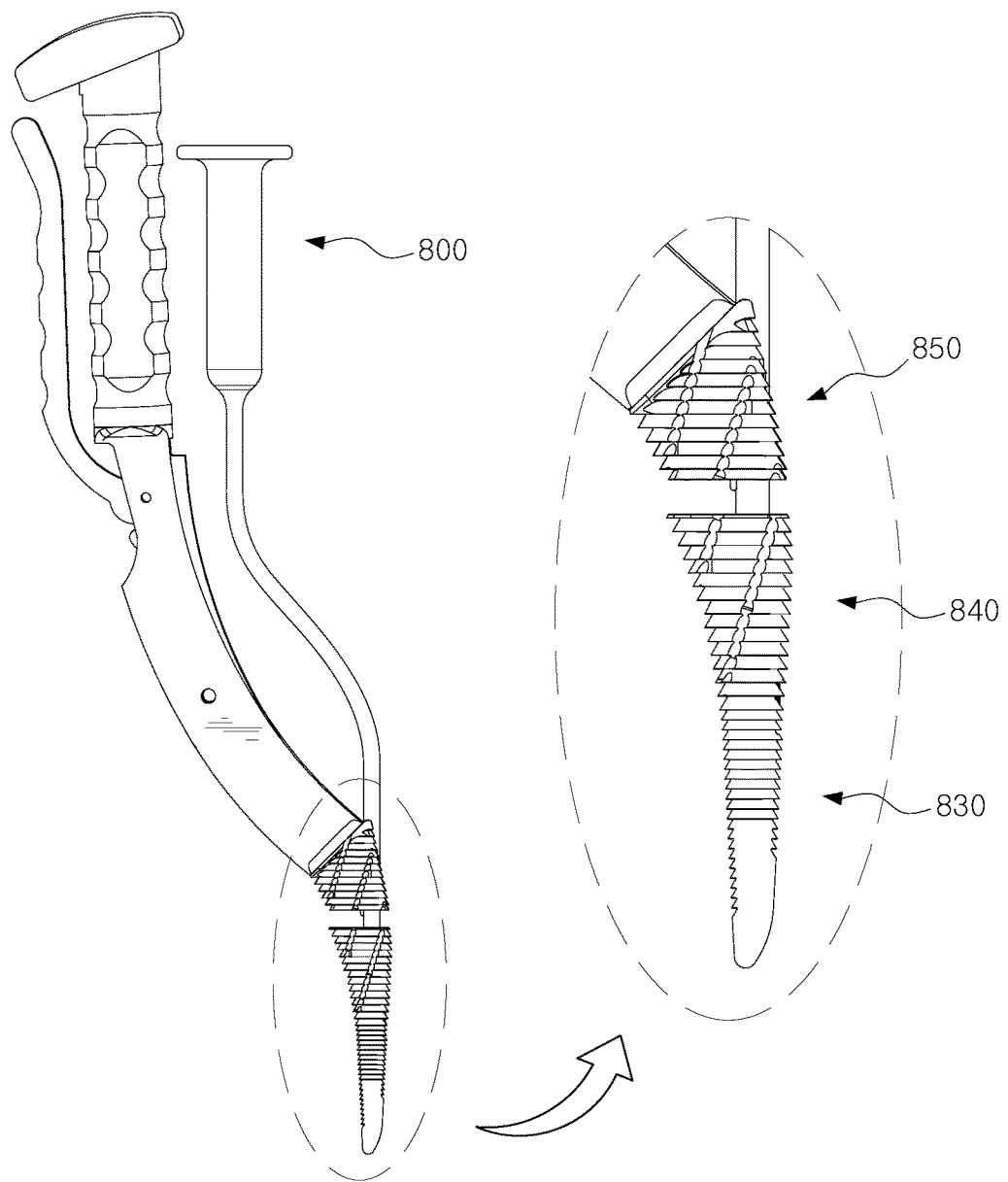

As shown in FIGS. 32 and 33, the protrusion 847 in the second cutting segment 840 is inserted in the protrusion receiving hole in the first cutting segment 830. In the same fashion, the protrusion 854 in the third cutting segment 850 is inserted in the protrusion receiving hole in the second cutting segment 840. Hence, when the two cutting segments are connected to each other, the protrusions and the protrusion receiving holes enable the cutting segments to be accurately coupled with each other.

Figure 34:
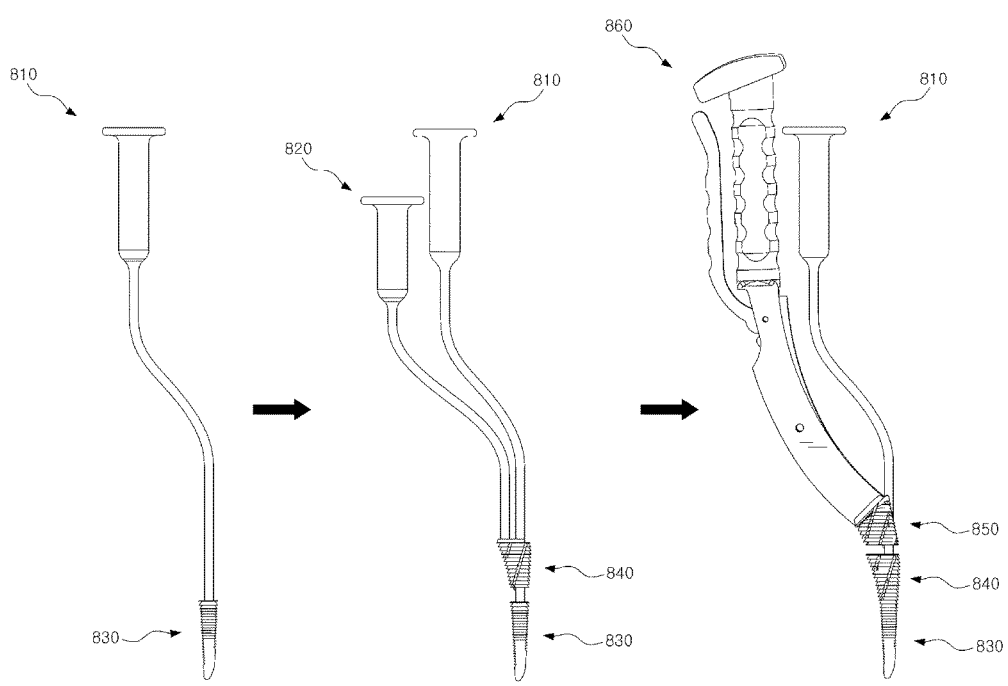
FIG. 34 shows an installation order of a broach according to the present invention.

FIG. 34 illustrates an installation of the broach according to the present invention. The first cutting segment 830 is mounted on the guide member 810. Subsequently, impaction force is applied to the strike portion 816 of the guide member 810 and the first cutting segment 830 is inserted inside the bone. Then the second cutting segment 840 mounted with the auxiliary guide member 820 is coupled with the first cutting segment along the guide member 810. The strike portion 826 of the auxiliary guide member 820 is struck to insert the second cutting segment 830, and then the auxiliary guide member 820 is detached. The third cutting segment 850 is coupled to the broach handle 860 by the fitting portion 856 and guided by the guide member 810 to be additionally inserted in the bone.

According to the broach of the present invention, a broach commonly formed as one body is divided into a plurality of broach segments, and the segments are seated in the femoral stem one by one. This makes the broach of the present invention function as the common broach since the size of the broach becomes the same with that of the broach formed as one body. Moreover, damage to the surroundings are avoided since most of the broach segments are placed inside the femoral canal as additional cutting segment is inserted after canal preparation by one cutting segment is finished.

Also, additional third, fourth cutting segments and so on may be included to be placed inside the femoral canal through the guide member based on need by using the aforementioned method. As each segment is prepared by dividing the prior lengthy broach into small pieces, the each segment is to have a shorter length compared to the prior broach. Since one segment is inserted in the bone and additional segments are subsequently inserted when necessary, muscle damage is fundamentally prevented.

Figure 35:
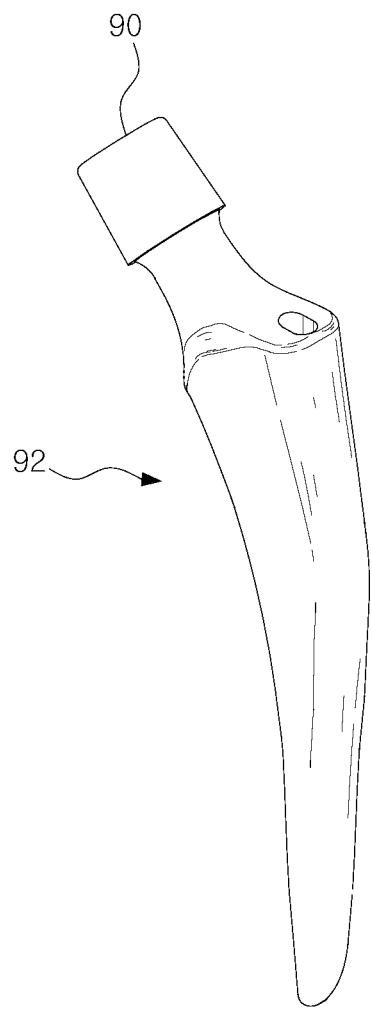
FIG. 35 shows a femoral stem mounted with a trunnion protector according to one embodiment of the present invention.
Figure 36:
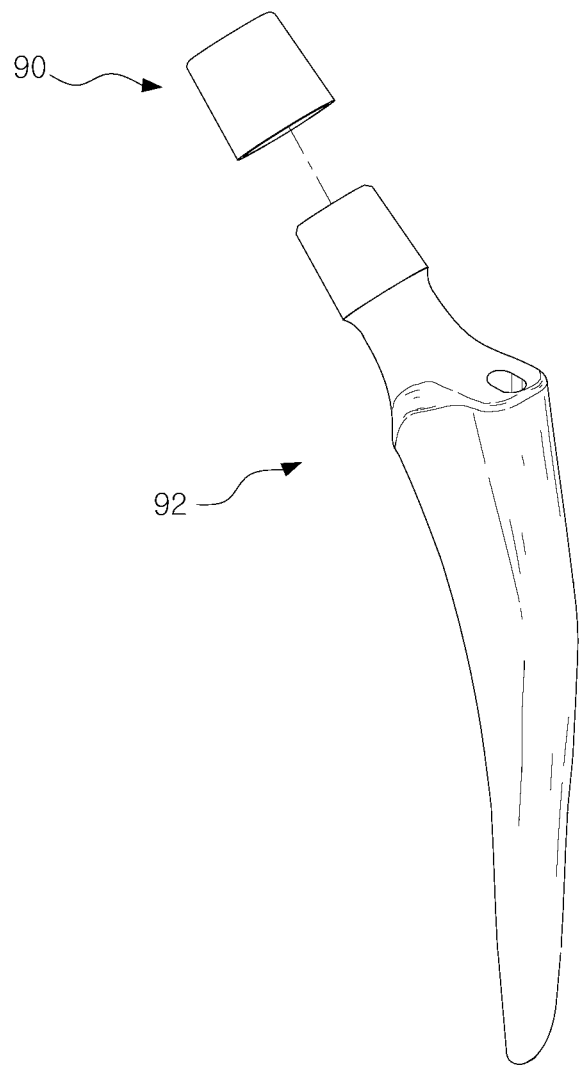
FIG. 36 shows an exploded view of FIG. 30.

As shown in FIGS. 35 and 36, the set of surgical instruments for an artificial hip joint implant may comprise a trunnion protector 90 for protecting a trunnion of the femoral stem.

Figure 37A:
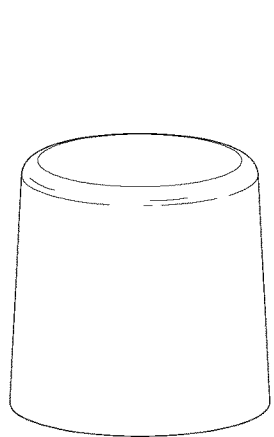
FIG. 37a shows a trunnion protector.
Figure 37B:
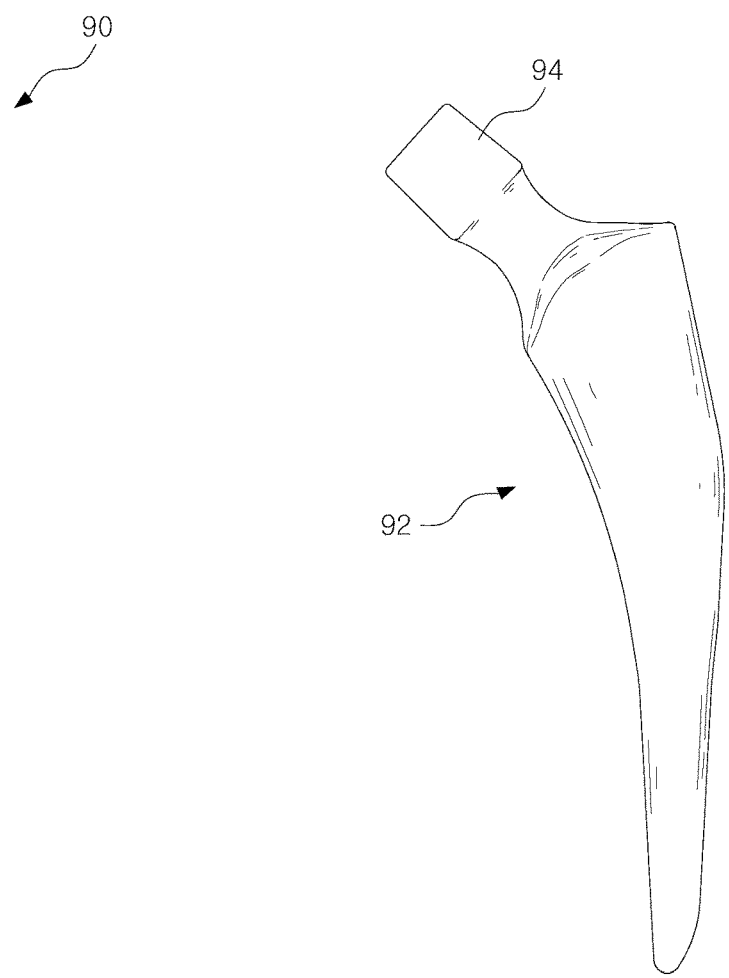
FIG. 37b shows a femoral stem from which a trunnion protector is removed.

As shown in FIGS. 37a and 37b, the trunnion protector 90 is a cone-shaped cap disposed on the outer face of the trunnion 94 of the femoral stem 92 and protects the femoral stem 92 by covering.

Figure 37C:
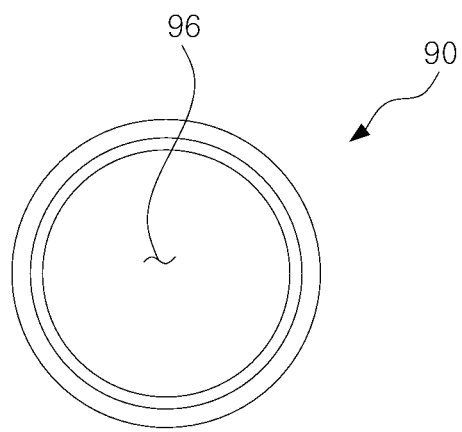

As shown in FIG. 37c, a receiving portion 96 which receives the trunnion 94 is formed at an inner side of the trunnion protector 90. Preferably, the receiving portion 96 is formed to have a shape complementary to the trunnion 94 of the femur such that the trunnion protector 90 is fixed by fit connection in the trunnion 94. Even in this case, since the trunnion protector 90 needs to be removed later, the protector 90 may be configured to be disposable or a modular type for easy removal.

Furthermore, the trunnion protector 90 may include a cleaning solution capable of removing both soluble and insoluble materials, material which does not leave behind fabrics, and a device generating optimal impaction forces.

Figure 38A:
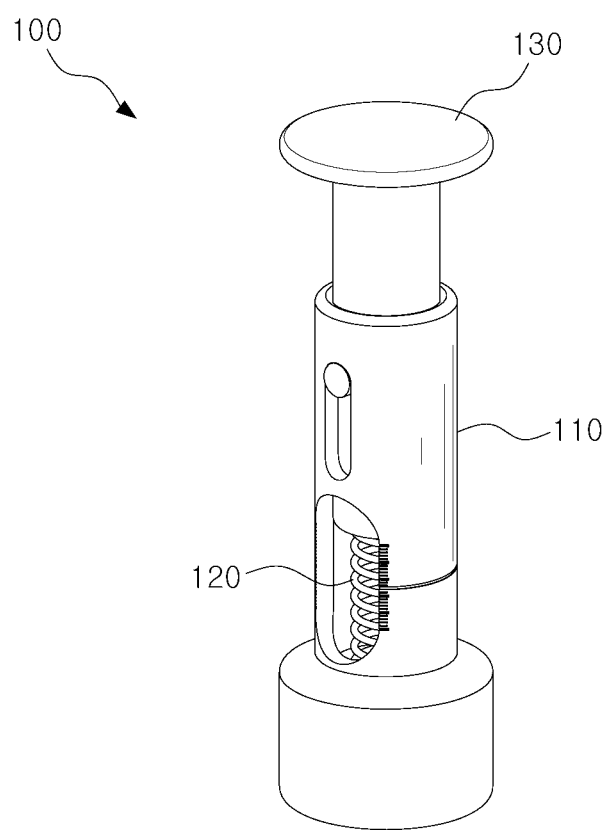
FIG. 38a shows a perspective view of an impaction measuring device in a stretched state according to another embodiment of the present invention.
Figure 38B:
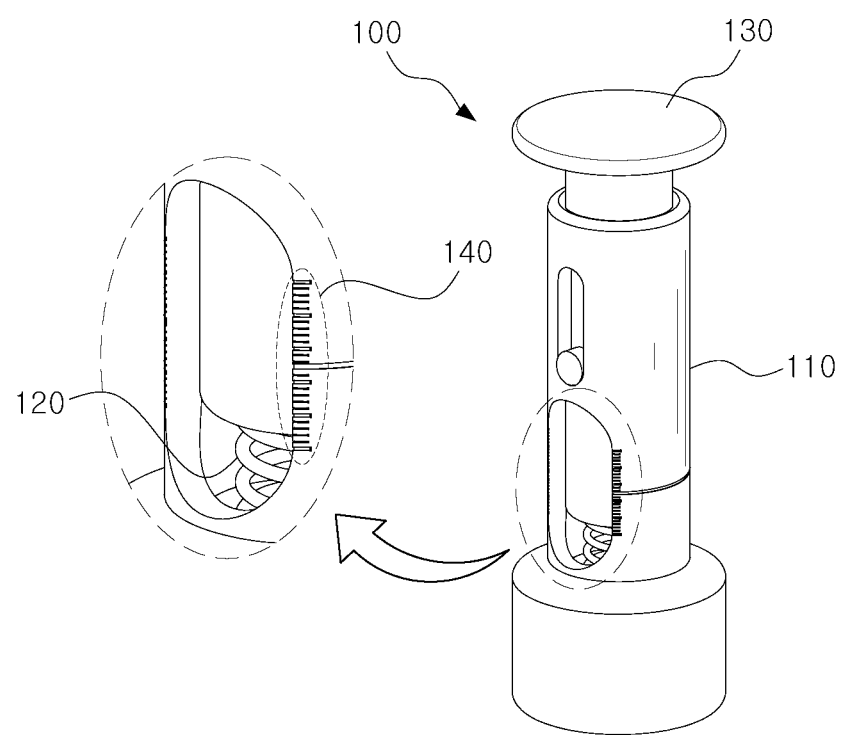
FIG. 38b shows a perspective view of an impaction measuring device in a compressed state according to another embodiment of the present invention.

As shown in FIGS. 38a and 38b, the set of surgical instruments for an artificial hip joint implant according to the present invention may comprise an impaction measuring device configured to measure impaction exerted on a modular head of a hip joint implant. When the modular head is inserted into the femoral stem, fracture of the modular head may occur if too much impaction force is applied, while premature separation of the modular head may occur if too weak impaction force is applied. The device is developed to prevent such problem by providing a surgeon with a sense about the level of impaction forces applied to the modular head before surgery. That is, according to the present invention, risk of surgical failure can be reduced by enabling the surgeon to measure the level of impaction force applied before insertion of the modular head in actual surgery. The impaction measuring device 100 may comprise a main body 110; a resisting body 120; and an impactor 130.

Figure 39:
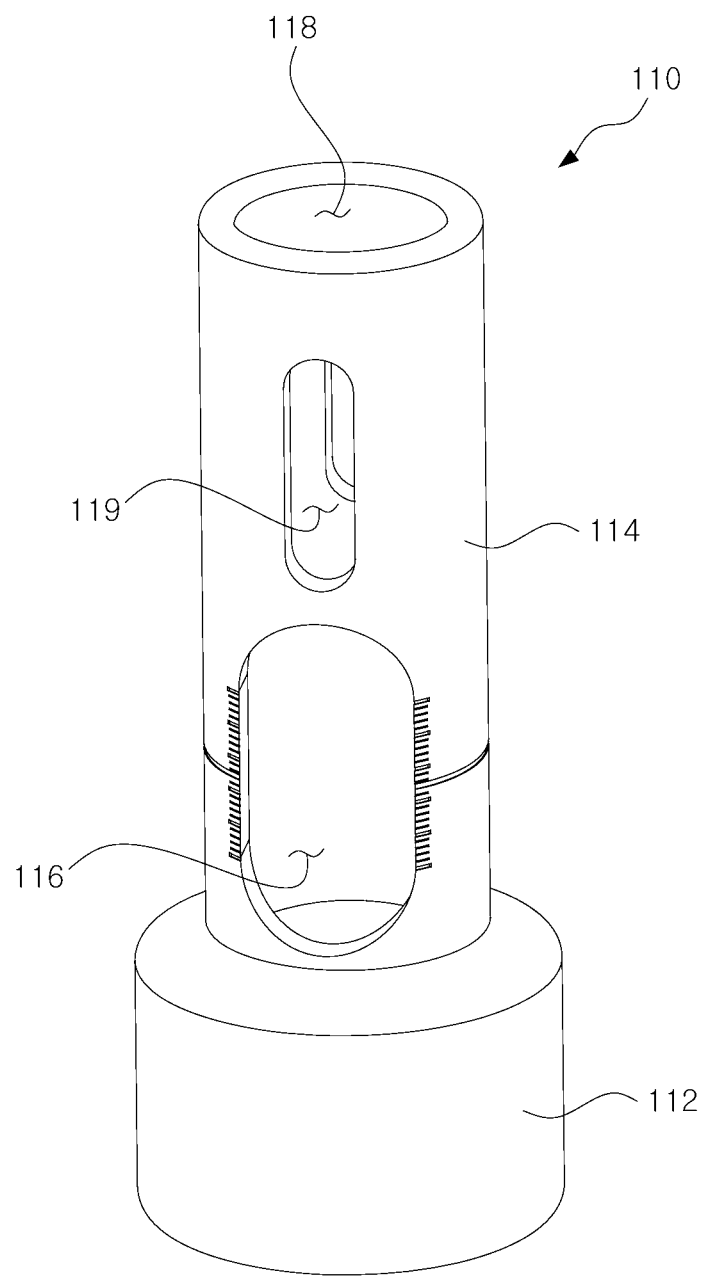
FIG. 39 shows a perspective view of a main body of an impaction measuring device according to another embodiment of the present invention.

Referring to FIGS. 38a, 38b, and 39, the main body 110 is installed on the ground, a table, or a flat surface to support the impaction measuring device 100. The main body 110 comprises a base portion 112 disposed to be fixed on the ground; and a cylinder portion 114 formed approximately perpendicular to the base portion 112 and receiving the resisting body 120 described below.

The base portion 112 is configured to be in parallel with the ground and is connected to one end of the resisting body 120. The cylinder portion 114 protrudes vertically from the base portion 112 and has a through-hole 118 to receive the resisting body 120 inside. That is, the cylinder portion 114 may be of a tubular shape, yet the shape of the cross section of the cylinder portion 114 may be rectangular, polygonal and so on, which means it is not limited to a circle.

A window 119 which limits the vertical movement of the impactor 130 is formed on the outer circumference of the cylinder portion 114. The window 119 is formed vertically in the cylinder portion 114, and the window 119 is formed by piercing certain parts of the cylinder portion 114. A protrusion 136 formed in the impactor 130 is configured to be movable within the window 119 as walls of the window 119 limits the movement of the protrusion 136.

Moreover, an opening 116 through which part of the connecting area between the impactor 130 and the resisting body 120 are observable is formed on the outer circumference of the cylinder portion 114. This is a means for reading the markings described below.

The resisting body 120 received inside the main body 110 is an element which resists deformation by the impaction and may be an elastic body, like a spring. The resisting body 120 may be mounted inside the through-hole 118 of the main body 110 and one end is fixed in the base portion 112. The other end of the resisting body 120 is connected to the impactor 130 described below.

Figure 40:
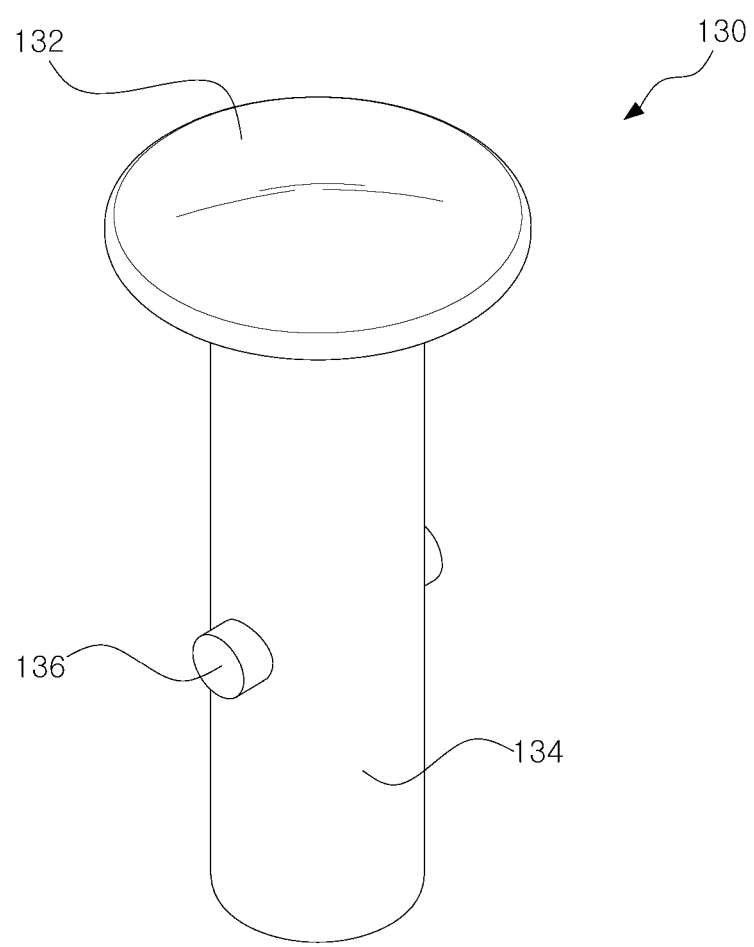
FIG. 40 shows a perspective view of an impactor of an impaction measuring device according to another embodiment of the present invention.

Referring to FIG. 40, the impactor 130 being an element conveying impaction forces applied from the external to the resisting body 120 includes a strike portion 132 configured to receive the impaction force and a rod portion 134 extending perpendicularly from the strike portion 132. The rod portion 134 of the impactor 130 is connected to the other end of the resisting body 120, and the impactor 130 and the resisting body 120 connected thereto move together when the impaction force is applied, received inside the main body 110 or the through-hole 118 of the main body 110. In other words, the impactor 130 and the resisting body 120 are movable together inside the main body 110.

FIGS. 38a and 38b illustrates the resisting body in a stretched state and a compressed state by the impaction force, respectively. A protrusion 136 may be included protruding radially outwardly from the rod portion 14 in the rod portion 134 of the impactor 130. The protrusion 136 is movable vertically inside the window 119 of the cylinder portion 114. As shown in FIG. 38a, when the protrusion 136 is positioned at the highest point of the window 19, the resisting body 120 is stretched the most. On the other hand, as shown in FIG. 38b, when the protrusion 136 is positioned at the lowest point of the window 119 the resisting body 120 is compressed the most by applied impaction force. The protrusion 136 allows the strike portion 132 connected to the resisting body 120 to be movable with respect to the main body 110.

The impaction measuring device 100 enables quantitative measurement of the impaction force by using the moving distance of the impactor 130 entering the receiving space of the main body 110, i.e., the amount of deformation of the resisting body 120. For objective measurement, provided is a display means, such as markings, which displays the magnitude of the impaction force dependent on the movement of the impactor 130.

That is, markings 140 may be displayed in the cylinder portion 114 for displaying the moving distance of the impactor portion 130. The opening 117 allows an end of the rod portion 134 of the impactor 130 disposed inside the cylinder portion 114. Then a marking where the end of the rod portion 134 and the markings 140 can be read.

The surgeon changes striking force and checks the measurement at each trial, obtained by using the moving distance displayed by the marking and spring constant of the resisting body and comes to understand the adequate amount of forces needed during actual surgery as the level of force can be converted into the quantitative measurements according to the present invention.

Therefore, according to the present invention, various levels of impaction forces are applied to the impaction measuring device and quantitative measurements can be obtained about the impaction forces, thereby making a proper amount of force to be applied to the modular head. In other words, fracture of the modular head is avoided by preventing application of too strong force during actual surgery and premature separation of the modular head can be prevented, which may happen when too weak force is applied.

In the above, the applicant described various embodiments of the present invention. It should be interpreted that such embodiments are merely examples which implement the technical idea and any modification or revision falls within the scope of the present invention if it implements the technical idea of the present invention, however.

REFERENCE NUMERALS

10: retractor
12: grip portion
14: rounded part
16: shield
18: coupling hole
20: tubular element
22: slit
24: end
30: gigli saw
42: bar member
44: mounting hole
50: reamer
52: cutting portion
54: flexible shaft
60: telescopic protector
62: first rod
64: first penetration hole
66: second rod
68: second penetration hole
70: third rod
72: third penetration hole
74: fourth rod
76: fourth penetration hole
80: broach
82: guide member
84: first cutting segment
86: second cutting segment
88: strike portion
90: trunnion protector
92: stem
94: trunnion
96: receiving portion
100: impaction measuring device
110: main body
112: base portion
114: cylinder portion
117: opening
118: through-hole
119: window
120: resisting body
130: impactor
132: strike portion
134: rod portion
136: protrusion
140: marking
402: capsule
404: femur
406: retractor
800: broach
810: guide member
812: shaft portion
813: screw
814: grip portion
815: coupling member
816: strike portion
817: insertion hole
819: slot
820: auxiliary guide member
822: shaft portion
823: end
824: grip portion
826: strike portion
830: first cutting segment
832: first cutout portion
834: upper face
836: protrusion receiving portion
840: second cutting segment
842: second cutout portion
844: upper face
846: hole
847: protrusion
848: protrusion receiving portion
850: third cutting segment
852: third cutout portion
854: protrusion
856: fitting part
860: broach handle

The invention claimed is:

1. A set of surgical instruments for an artificial hip joint implant, comprising a broach for enlarging a hole for installing a femoral stem in a femur, wherein the broach comprises a modular broach, the modular broach comprising:
a guide member;
an auxiliary guide member configured to be connected to the guide member;
a first cutting segment configured to be installed at an end of the guide member; and
a second cutting segment configured to be installed on the auxiliary guide member,
wherein the first cutting segment includes a first cutout portion in which at least part of the volume at an upper side of the first cutting segment is cut out,
wherein the second cutting segment includes a second cutout portion where at least part of the volume of the second cutting segment is cut out at an upper part of the second cutting segment and the guide member is configured to be received in the second cut out portion.

2. The set of surgical instruments of claim 1, wherein the guide member and the first cutting segment are coupled by a screw connection along a horizontal direction.

3. The set of surgical instruments of claim 1, wherein a shape of a circumference of the first cutout portion is formed substantially the same with a shape of a circumference of the guide member and the circumferences include a straight portion.

4. The set of surgical instruments of claim 1, wherein a protrusion receiving portion is formed in a part where the first cutout portion contacts with a circumference of the first cutting segment.

5. The set of surgical instruments of claim 1, wherein the second cutting segment includes a protrusion protruding in a lower part of the second cutting segment.

6. The set of surgical instruments of claim 1,
wherein the guide member and the auxiliary guide member are coupled by a coupling member and the coupling member is mounted on an upper face of the second cutting segment and includes an insertion hole at one side and a slot formed at another side, wherein the slot has one side open to receive the guide member.

7. The set of surgical instruments of claim 6,
wherein an end of the auxiliary guide member has a hemispherical shape and is coupled to a hole formed in the second cutting segment.

\* \* \* \* \*